United States Patent
Morita et al.

(10) Patent No.: US 10,000,760 B2
(45) Date of Patent: Jun. 19, 2018

(54) YEAST WITH HIGH CONTENT OF ABU, γ-GLU-ABU, AND/OR γ-GLU-ABU-GLY

(71) Applicant: AJINOMOTO CO., INC., Tokyo (JP)

(72) Inventors: Misato Morita, Kawasaki (JP); Hiroaki Nishiuchi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days. days.

(21) Appl. No.: 14/976,636

(22) Filed: Dec. 21, 2015

(65) Prior Publication Data

US 2016/0177323 A1 Jun. 23, 2016

Related U.S. Application Data

(63) Continuation of application No. PCT/JP2014/068283, filed on Jul. 9, 2014.

(30) Foreign Application Priority Data

Jul. 12, 2013 (JP) ................................ 2013-146315
Jan. 10, 2014 (JP) ................................ 2014-003606

(51) Int. Cl.
| | |
|---|---|
| C12N 1/14 | (2006.01) |
| C12N 15/00 | (2006.01) |
| C12N 9/88 | (2006.01) |
| C12N 9/10 | (2006.01) |
| C12N 9/16 | (2006.01) |
| C12P 13/00 | (2006.01) |
| C07H 21/04 | (2006.01) |
| C12N 15/81 | (2006.01) |
| C12N 1/16 | (2006.01) |
| C12P 13/04 | (2006.01) |
| C12P 13/14 | (2006.01) |
| A23L 27/21 | (2016.01) |
| A23L 27/23 | (2016.01) |
| A23L 33/14 | (2016.01) |
| A23L 33/145 | (2016.01) |

(52) U.S. Cl.
CPC ............ *C12N 15/815* (2013.01); *A23L 27/21* (2016.08); *A23L 27/23* (2016.08); *A23L 33/14* (2016.08); *A23L 33/145* (2016.08); *C12N 1/16* (2013.01); *C12N 9/1025* (2013.01); *C12N 9/88* (2013.01); *C12N 15/81* (2013.01); *C12P 13/04* (2013.01); *C12P 13/14* (2013.01); *C12Y 202/01006* (2013.01); *A23V 2002/00* (2013.01)

(58) Field of Classification Search
None
See application file for complete search history.

(56) References Cited

U.S. PATENT DOCUMENTS

| | | |
|---|---|---|
| 2009/0087515 A1 | 4/2009 | Nakao et al. |
| 2013/0280381 A1 | 10/2013 | Nishiuchi et al. |

FOREIGN PATENT DOCUMENTS

| | | |
|---|---|---|
| JP | 11-235176 A | 8/1999 |
| JP | 2009-527218 A | 7/2009 |
| WO | WO 2012/046731 A1 | 4/2012 |

OTHER PUBLICATIONS

Kingsbury. Cytocidal amino acid starvation of *Saccharomyces cerevisiae* and Candida albicans acetolactate synthase (ilv2{Delta}) mutants is influenced by the carbon source and rapamycin. Microbiology. Mar. 2010;156(Pt 3):929-39. doi: 10.1099/mic.0.034348-0. Epub Dec. 17, 2009.*
Stewart. Biotechnology and Genetic Engineering Reviews, 14:67-143, 1997.*
Nishiuchi. Machine Translation of WO 2012/046731. 2016.*
International Preliminary Report issued in PCT/JP2014/068283 dated Jan. 12, 2016.
International Search Report dated Oct. 7, 2014, in International Application No. PCT/JP2014/068283, filed Jul. 9, 2014 (2 pages).
Liu, Z., et al., Constructing an Amylolytic Brewing Yeast *Saccharomyces pastorianus* Suitable for Accelerated Brewing, Journal of Bioscience and Bioengineering, 2004, vol. 98, No. 6, p. 414-419, p. 415, p. 416.
Wang, Z-Y., et al., Construction of self-cloning industrial brewing yeast with high-glutathione and low-diacetyl production, International Journal of Food Science & Technology, 2008, vol. 43, p. 989-994, p. 990-992.
Larossa, Robert A., et al., Bioessays., 1987, vol. 7, No. 3, pp. 125-130.

* cited by examiner

*Primary Examiner* — Yong D Pak
(74) *Attorney, Agent, or Firm* — Oblon, McClelland, Maier & Neustadt, L.L.P.

(57) ABSTRACT

Yeast and a yeast extract with a high content of Abu, γ-Glu-Abu, and/or γ-Glu-Abu-Gly are provided. By modifying yeast so that intracellular acetolactate synthase activity is reduced, yeast with a high content of Abu, γ-Glu-Abu, and/or γ-Glu-Abu-Gly is obtained. An yeast extract is prepared by using the yeast obtained in such a manner as a raw material.

20 Claims, 4 Drawing Sheets

[Fig. 1]
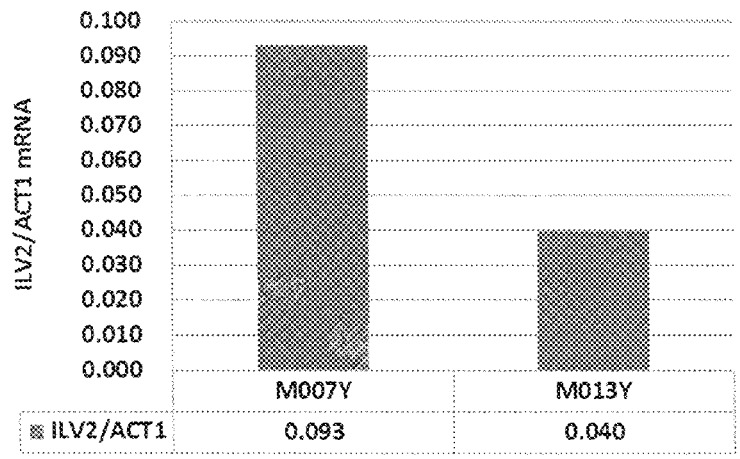
[Fig. 2]
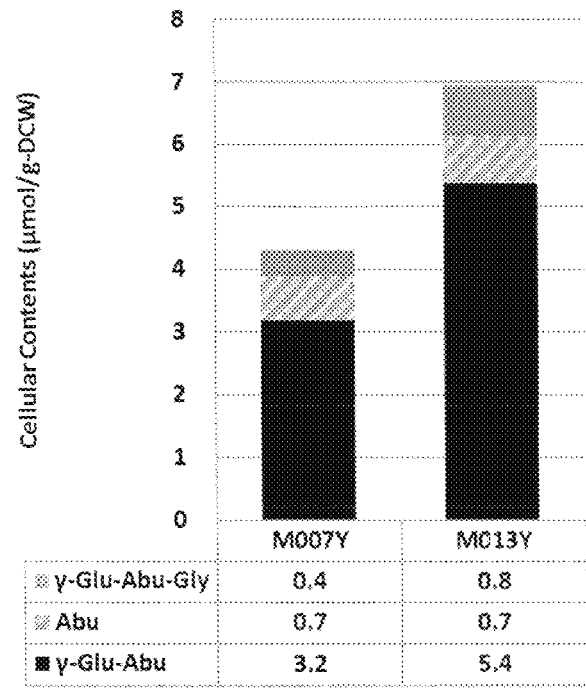

[Fig. 3]
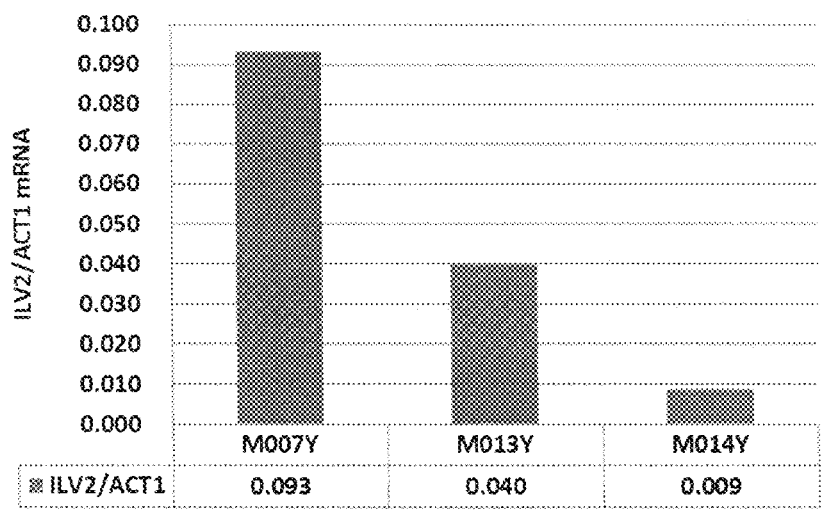
[Fig. 4]
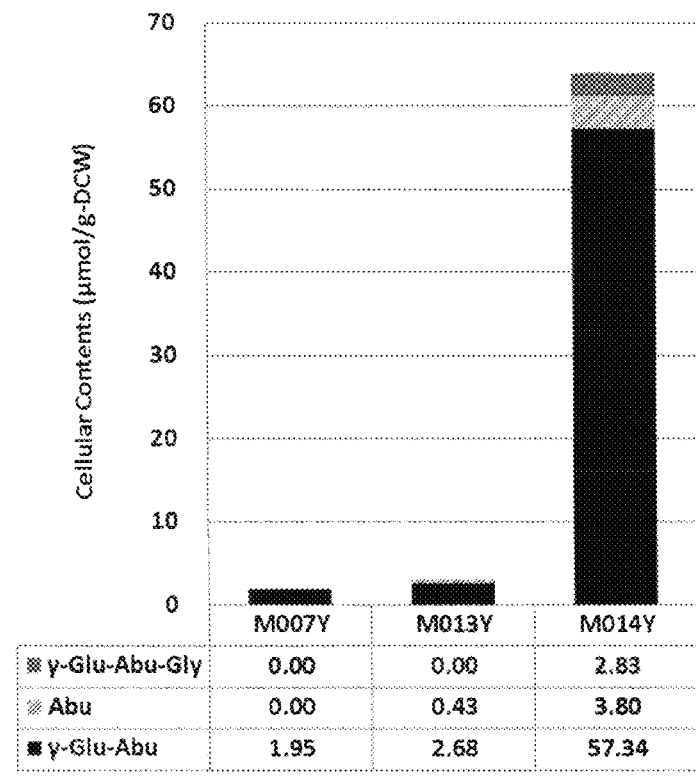

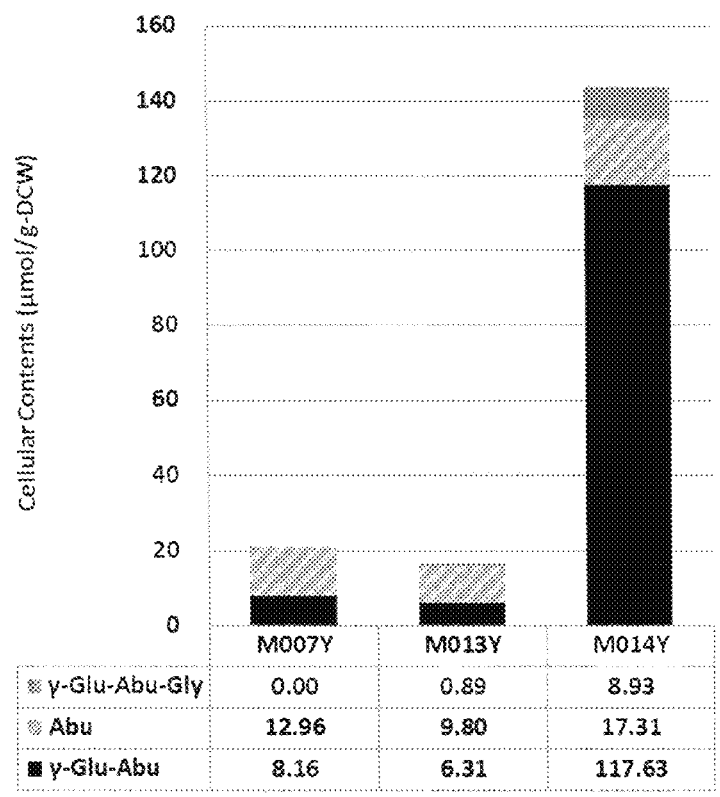
[Fig. 5]

[Fig. 6]
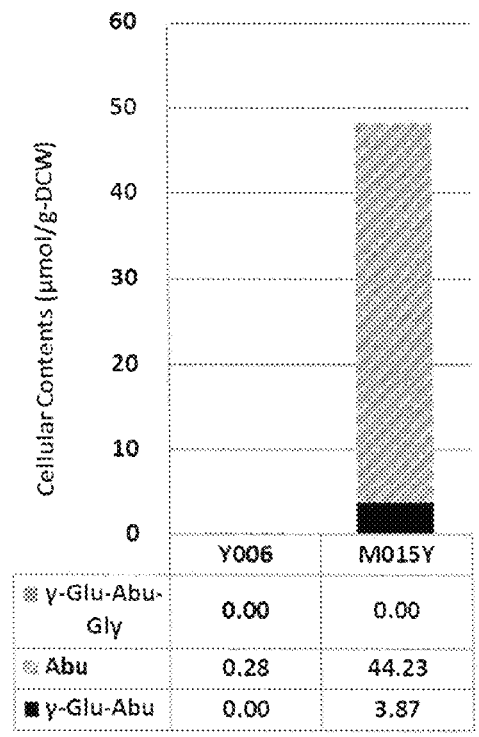
[Fig. 7]
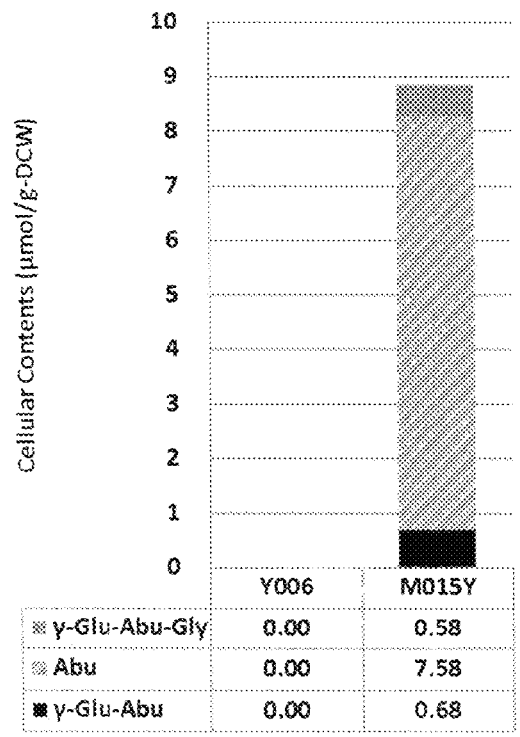

SEQUENCE LISTING

<160> NUMBER OF SEQ ID NOS: 26

<210> SEQ ID NO 1
<211> LENGTH: 100
<212> TYPE: DNA
<213> ORGANISM: Artificial Sequence

```
<220> FEATURE:
<223> OTHER INFORMATION: primer

<400> SEQUENCE: 1
gccaggcggt tgatactttg tgcagatttc ataccggctg tcgctattat tactgatgaa      60
ttggctctct ttttgtttaa tcttaaccca actgcacaga                            100

<210> SEQ ID NO 2
<211> LENGTH: 100
<212> TYPE: DNA
<213> ORGANISM: Artificial Sequence
<220> FEATURE:
<223> OTHER INFORMATION: primer

<400> SEQUENCE: 2
ttggatgcat ctaatggggc accagtagcg agtgttctga tggagaattt ccccaacttc      60
aaggaatgtc tctgcaacat ttgtttatgt gtgtttattc                            100

<210> SEQ ID NO 3
<211> LENGTH: 100
<212> TYPE: DNA
<213> ORGANISM: Artificial Sequence
<220> FEATURE:
<223> OTHER INFORMATION: primer

<400> SEQUENCE: 3
gagtactaat caccgcgaac ggaaactaat gagtcctctg cgcggagaca tgattccgca      60
tgggcggctc ctgttaagcc tcttaaccca actgcacaga                            100

<210> SEQ ID NO 4
<211> LENGTH: 100
<212> TYPE: DNA
<213> ORGANISM: Artificial Sequence
<220> FEATURE:
<223> OTHER INFORMATION: primer

<400> SEQUENCE: 4
tatttcaaga aaaattgtgc agaagccttt ccggggaaga attgacgtaa taatggtgtt      60
ttattgtaga ctatcgacat ttgtttatgt gtgtttattc                            100

<210> SEQ ID NO 5
<211> LENGTH: 100
<212> TYPE: DNA
<213> ORGANISM: Artificial Sequence
<220> FEATURE:
<223> OTHER INFORMATION: primer

<400> SEQUENCE: 5
ctctttattg catattatct ctgctatttt gtgacgttca attttaattg acgcgaaaaa      60
gaaaaaataa gaagggcaaa tcttaaccca actgcacaga                            100

<210> SEQ ID NO 6
<211> LENGTH: 100
<212> TYPE: DNA
<213> ORGANISM: Artificial Sequence
<220> FEATURE:
<223> OTHER INFORMATION: primer

<400> SEQUENCE: 6
aggttcaatc cagacacttt ggactgttta ccttgccgaa caaccgtaca taatggttgc      60
tttagtagag tagctgacat ttgtttatgt gtgtttattc                            100
```

```
<210> SEQ ID NO 7
<211> LENGTH: 99
<212> TYPE: DNA
<213> ORGANISM: Artificial Sequence
<220> FEATURE:
<223> OTHER INFORMATION: primer

<400> SEQUENCE: 7
tatctggttg atatatatgc tatcatttat tttcttatca agtttccaaa tttctaatcc      60
tttctccacc atccctaatt cttaacccaa ctgcacaga                            99

<210> SEQ ID NO 8
<211> LENGTH: 99
<212> TYPE: DNA
<213> ORGANISM: Artificial Sequence
<220> FEATURE:
<223> OTHER INFORMATION: primer

<400> SEQUENCE: 8
ggtgtgttgc ggtatgctat atgttgaaag caacgcttaa tagcgaagtt ttttagcgta      60
gattgtctga tcatgttttt tctccttgac gttaaagta                            99

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
ctttacaggg caagtcccaa cta                                             23

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
cgacgtcagc ctcttggaa                                                  19

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tcgttccaat ttacgctggt t                                               21

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
cggccaaatc gattctcaa                                                  19
```

<210> SEQ ID NO 13
<211> LENGTH: 97
<212> TYPE: DNA
<213> ORGANISM: Artificial Sequence
<220> FEATURE:
<223> OTHER INFORMATION: primer

<400> SEQUENCE: 13
gttacaatag aaagtatttt acaaaatcta aacccttga gctaagagga gataaataca    60
acagaatcaa ttttcaaaag ggcaacggtt catcatc                             97

<210> SEQ ID NO 14
<211> LENGTH: 97
<212> TYPE: DNA
<213> ORGANISM: Artificial Sequence
<220> FEATURE:
<223> OTHER INFORMATION: primer

<400> SEQUENCE: 14
tataagaagc acgattaaat aataataaag tctgcatttt ttactgaaaa tgcttttgaa    60
ataaatgttt ttgaaatatt agatatatat acgccag                             97

<210> SEQ ID NO 15
<211> LENGTH: 2064
<212> TYPE: DNA
<213> ORGANISM: Saccharomyces cerevisiae
<220> FEATURE:
<221> NAME/KEY: CDS
<222> LOCATION: (1)..(2064)

<400> SEQUENCE: 15

| | | | | | | | | | | | | | | | |
|---|---|---|---|---|---|---|---|---|---|---|---|---|---|---|---|
| atg | atc | aga | caa | tct | acg | cta | aaa | aac | ttc | gct | att | aag | cgt | tgc | ttt | 48 |
| Met | Ile | Arg | Gln | Ser | Thr | Leu | Lys | Asn | Phe | Ala | Ile | Lys | Arg | Cys | Phe | |
| 1 | | | | 5 | | | | | 10 | | | | | 15 | | |
| caa | cat | ata | gca | tac | cgc | aac | aca | cct | gcc | atg | aga | tca | gta | gct | ctc | 96 |
| Gln | His | Ile | Ala | Tyr | Arg | Asn | Thr | Pro | Ala | Met | Arg | Ser | Val | Ala | Leu | |
| | | | 20 | | | | | 25 | | | | | 30 | | | |
| gcg | cag | cgc | ttt | tat | agt | tcg | tct | tcc | cgt | tat | tac | agt | gcg | tct | cca | 144 |
| Ala | Gln | Arg | Phe | Tyr | Ser | Ser | Ser | Ser | Arg | Tyr | Tyr | Ser | Ala | Ser | Pro | |
| | | 35 | | | | | 40 | | | | | 45 | | | | |
| tta | cca | gcc | tct | aaa | agg | cca | gag | cct | gct | cca | agt | ttc | aat | gtt | gat | 192 |
| Leu | Pro | Ala | Ser | Lys | Arg | Pro | Glu | Pro | Ala | Pro | Ser | Phe | Asn | Val | Asp | |
| | 50 | | | | | 55 | | | | | 60 | | | | | |
| cca | tta | gaa | cag | ccc | gct | gaa | cct | tca | aaa | ttg | gct | aag | aaa | cta | cgc | 240 |
| Pro | Leu | Glu | Gln | Pro | Ala | Glu | Pro | Ser | Lys | Leu | Ala | Lys | Lys | Leu | Arg | |
| 65 | | | | | 70 | | | | | 75 | | | | | 80 | |
| gct | gag | cct | gac | atg | gat | acc | tct | ttc | gtc | ggt | tta | act | ggt | ggt | caa | 288 |
| Ala | Glu | Pro | Asp | Met | Asp | Thr | Ser | Phe | Val | Gly | Leu | Thr | Gly | Gly | Gln | |
| | | | | 85 | | | | | 90 | | | | | 95 | | |
| ata | ttt | aac | gaa | atg | atg | tcc | aga | caa | aac | gtt | gat | act | gta | ttt | ggt | 336 |
| Ile | Phe | Asn | Glu | Met | Met | Ser | Arg | Gln | Asn | Val | Asp | Thr | Val | Phe | Gly | |
| | | | | 100 | | | | | 105 | | | | | 110 | | |
| tat | cca | ggt | ggt | gct | atc | cta | cct | gtt | tac | gat | gcc | att | cat | aac | agt | 384 |
| Tyr | Pro | Gly | Gly | Ala | Ile | Leu | Pro | Val | Tyr | Asp | Ala | Ile | His | Asn | Ser | |
| | | | 115 | | | | | 120 | | | | | 125 | | | |
| gat | aaa | ttc | aac | ttc | gtt | ctt | cca | aaa | cac | gaa | caa | ggt | gcc | ggt | cac | 432 |
| Asp | Lys | Phe | Asn | Phe | Val | Leu | Pro | Lys | His | Glu | Gln | Gly | Ala | Gly | His | |
| | | 130 | | | | | 135 | | | | | 140 | | | | |
| atg | gca | gaa | ggc | tac | gcc | aga | gct | tct | ggt | aaa | cca | ggt | gtt | gtc | ttg | 480 |
| Met | Ala | Glu | Gly | Tyr | Ala | Arg | Ala | Ser | Gly | Lys | Pro | Gly | Val | Val | Leu | |
| 145 | | | | | 150 | | | | | 155 | | | | | 160 | |

```
gtt act tct ggg cca ggt gcc acc aat gtc gtt act cca atg gca gat         528
Val Thr Ser Gly Pro Gly Ala Thr Asn Val Val Thr Pro Met Ala Asp
            165                 170                 175 gcc ttt gca gac ggg att cca atg gtt gtc ttt aca ggg caa gtc cca         576
Ala Phe Ala Asp Gly Ile Pro Met Val Val Phe Thr Gly Gln Val Pro
            180                 185                 190 act agt gct atc ggt act gat gct ttc caa gag gct gac gtc gtt ggt         624
Thr Ser Ala Ile Gly Thr Asp Ala Phe Gln Glu Ala Asp Val Val Gly
            195                 200                 205 att tct aga tct tgt acg aaa tgg aat gtc atg gtc aag tcc gtg gaa         672
Ile Ser Arg Ser Cys Thr Lys Trp Asn Val Met Val Lys Ser Val Glu
            210                 215                 220 gaa ttg cca ttg cgt att aac gag gct ttt gaa att gcc acg agc ggt         720
Glu Leu Pro Leu Arg Ile Asn Glu Ala Phe Glu Ile Ala Thr Ser Gly
225                 230                 235                 240 aga ccg gga cca gtc ttg gtc gat tta cca aag gat gtt aca gca gct         768
Arg Pro Gly Pro Val Leu Val Asp Leu Pro Lys Asp Val Thr Ala Ala
                    245                 250                 255 atc tta aga aat cca att cca aca aaa aca act ctt cca tca aac gca         816
Ile Leu Arg Asn Pro Ile Pro Thr Lys Thr Thr Leu Pro Ser Asn Ala
                260                 265                 270 cta aac caa tta acc agt cgc gca caa gat gaa ttt gtc atg caa agt         864
Leu Asn Gln Leu Thr Ser Arg Ala Gln Asp Glu Phe Val Met Gln Ser
            275                 280                 285 atc aat aaa gca gca gat ttg atc aac ttg gca aag aaa cct gtc tta         912
Ile Asn Lys Ala Ala Asp Leu Ile Asn Leu Ala Lys Lys Pro Val Leu
290                 295                 300 tac gtc ggt gct ggt att tta aac cat gca gat ggt cca aga tta cta         960
Tyr Val Gly Ala Gly Ile Leu Asn His Ala Asp Gly Pro Arg Leu Leu
305                 310                 315                 320 aaa gaa tta agt gac cgt gct caa ata cct gtc acc act act tta caa        1008
Lys Glu Leu Ser Asp Arg Ala Gln Ile Pro Val Thr Thr Thr Leu Gln
                325                 330                 335 ggt tta ggt tca ttc gac caa gaa gat cca aaa tca ttg gat atg ctt        1056
Gly Leu Gly Ser Phe Asp Gln Glu Asp Pro Lys Ser Leu Asp Met Leu
            340                 345                 350 ggt atg cac ggt tgt gct act gcc aac ctg gca gtg caa aat gcc gac        1104
Gly Met His Gly Cys Ala Thr Ala Asn Leu Ala Val Gln Asn Ala Asp
            355                 360                 365 ttg ata att gca gtt ggt gct aga ttc gac gac cgt gtc act ggt aat        1152
Leu Ile Ile Ala Val Gly Ala Arg Phe Asp Asp Arg Val Thr Gly Asn
            370                 375                 380 att tct aaa ttc gct cca gaa gct cgt cgt gca gct gcc gag ggt aga        1200
Ile Ser Lys Phe Ala Pro Glu Ala Arg Arg Ala Ala Ala Glu Gly Arg
385                 390                 395                 400 ggt ggt att att cat ttc gag gtt agt cca aaa aac ata aac aag gtt        1248
Gly Gly Ile Ile His Phe Glu Val Ser Pro Lys Asn Ile Asn Lys Val
                405                 410                 415 gtt caa act caa ata gca gtg gaa ggt gat gct acg acc aat ctg ggc        1296
Val Gln Thr Gln Ile Ala Val Glu Gly Asp Ala Thr Thr Asn Leu Gly
            420                 425                 430 aaa atg atg tca aag att ttc cca gtt aag gag agg tct gaa tgg ttt        1344
Lys Met Met Ser Lys Ile Phe Pro Val Lys Glu Arg Ser Glu Trp Phe
            435                 440                 445 gct caa ata aat aaa tgg aag aag gaa tac cca tac gct tat atg gag        1392
Ala Gln Ile Asn Lys Trp Lys Lys Glu Tyr Pro Tyr Ala Tyr Met Glu
450                 455                 460 gag act cca gga tct aaa att aaa cca cag acg gtt ata aag aaa cta        1440
Glu Thr Pro Gly Ser Lys Ile Lys Pro Gln Thr Val Ile Lys Lys Leu
465                 470                 475                 480
```

-continued

| | | |
|---|---|---|
| tcc aag gtt gcc aac gac aca gga aga cat gtc att gtt aca acg ggt<br>Ser Lys Val Ala Asn Asp Thr Gly Arg His Val Ile Val Thr Thr Gly<br>485 490 495 | | 1488 |
| gtg ggg caa cat caa atg tgg gct gct caa cac tgg aca tgg aga aat<br>Val Gly Gln His Gln Met Trp Ala Ala Gln His Trp Thr Trp Arg Asn<br>500 505 510 | | 1536 |
| cca cat act ttc atc aca tca ggt ggt tta ggt acg atg ggt tac ggt<br>Pro His Thr Phe Ile Thr Ser Gly Gly Leu Gly Thr Met Gly Tyr Gly<br>515 520 525 | | 1584 |
| ctc cct gcc gcc atc ggt gct caa gtt gca aag cca gaa tct ttg gtt<br>Leu Pro Ala Ala Ile Gly Ala Gln Val Ala Lys Pro Glu Ser Leu Val<br>530 535 540 | | 1632 |
| att gac att gat ggt gac gca tcc ttt aac atg act cta acg gaa ttg<br>Ile Asp Ile Asp Gly Asp Ala Ser Phe Asn Met Thr Leu Thr Glu Leu<br>545 550 555 560 | | 1680 |
| agt tct gcc gtt caa gct ggt act cca gtg aag att ttg att ttg aac<br>Ser Ser Ala Val Gln Ala Gly Thr Pro Val Lys Ile Leu Ile Leu Asn<br>565 570 575 | | 1728 |
| aat gaa gag caa ggt atg gtt act caa tgg caa tcc ctg ttc tac gaa<br>Asn Glu Glu Gln Gly Met Val Thr Gln Trp Gln Ser Leu Phe Tyr Glu<br>580 585 590 | | 1776 |
| cat cgt tat tcc cac aca cat caa ttg aac cct gat ttc ata aaa cta<br>His Arg Tyr Ser His Thr His Gln Leu Asn Pro Asp Phe Ile Lys Leu<br>595 600 605 | | 1824 |
| gcg gag gct atg ggt tta aaa ggt tta aga gtc aag aag caa gag gaa<br>Ala Glu Ala Met Gly Leu Lys Gly Leu Arg Val Lys Lys Gln Glu Glu<br>610 615 620 | | 1872 |
| ttg gac gct aag ttg aaa gaa ttc gtt tct acc aag ggc cca gtt ttg<br>Leu Asp Ala Lys Leu Lys Glu Phe Val Ser Thr Lys Gly Pro Val Leu<br>625 630 635 640 | | 1920 |
| ctt gaa gtg gaa gtt gat aaa aaa gtt cct gtt ttg cca atg gtg gca<br>Leu Glu Val Glu Val Asp Lys Lys Val Pro Val Leu Pro Met Val Ala<br>645 650 655 | | 1968 |
| ggt ggt agc ggt cta gac gag ttc ata aat ttt gac cca gaa gtt gaa<br>Gly Gly Ser Gly Leu Asp Glu Phe Ile Asn Phe Asp Pro Glu Val Glu<br>660 665 670 | | 2016 |
| aga caa cag act gaa tta cgt cat aag cgt aca ggc ggt aag cac tga<br>Arg Gln Gln Thr Glu Leu Arg His Lys Arg Thr Gly Gly Lys His<br>675 680 685 | | 2064 |

<210> SEQ ID NO 16
<211> LENGTH: 687
<212> TYPE: PRT
<213> ORGANISM: Saccharomyces cerevisiae

<400> SEQUENCE: 16

Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

```
Ile Phe Asn Glu Met Met Ser Arg Gln Asn Val Asp Thr Val Phe Gly
            100                 105                 110

Tyr Pro Gly Gly Ala Ile Leu Pro Val Tyr Asp Ala Ile His Asn Ser
        115                 120                 125

Asp Lys Phe Asn Phe Val Leu Pro Lys His Glu Gln Gly Ala Gly His
    130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175

Ala Phe Ala Asp Gly Ile Pro Met Val Val Phe Thr Gly Gln Val Pro
            180                 185                 190

Thr Ser Ala Ile Gly Thr Asp Ala Phe Gln Glu Ala Asp Val Val Gly
        195                 200                 205

Ile Ser Arg Ser Cys Thr Lys Trp Asn Val Met Val Lys Ser Val Glu
210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
            260                 265                 270

Leu Asn Gln Leu Thr Ser Arg Ala Gln Asp Glu Phe Val Met Gln Ser
        275                 280                 285

Ile Asn Lys Ala Ala Asp Leu Ile Asn Leu Ala Lys Lys Pro Val Leu
290                 295                 300

Tyr Val Gly Ala Gly Ile Leu Asn His Ala Asp Gly Pro Arg Leu Leu
305                 310                 315                 320

Lys Glu Leu Ser Asp Arg Ala Gln Ile Pro Val Thr Thr Thr Leu Gln
                325                 330                 335

Gly Leu Gly Ser Phe Asp Gln Glu Asp Pro Lys Ser Leu Asp Met Leu
            340                 345                 350

Gly Met His Gly Cys Ala Thr Ala Asn Leu Ala Val Gln Asn Ala Asp
        355                 360                 365

Leu Ile Ile Ala Val Gly Ala Arg Phe Asp Asp Arg Val Thr Gly Asn
370                 375                 380

Ile Ser Lys Phe Ala Pro Glu Ala Arg Ala Ala Glu Gly Arg
385                 390                 395                 400

Gly Gly Ile Ile His Phe Glu Val Ser Pro Lys Asn Ile Asn Lys Val
                405                 410                 415

Val Gln Thr Gln Ile Ala Val Glu Gly Asp Ala Thr Thr Asn Leu Gly
            420                 425                 430

Lys Met Met Ser Lys Ile Phe Pro Val Lys Glu Arg Ser Glu Trp Phe
        435                 440                 445

Ala Gln Ile Asn Lys Trp Lys Lys Glu Tyr Pro Tyr Ala Tyr Met Glu
450                 455                 460

Glu Thr Pro Gly Ser Lys Ile Lys Pro Gln Thr Val Ile Lys Lys Leu
465                 470                 475                 480

Ser Lys Val Ala Asn Asp Thr Gly Arg His Val Ile Val Thr Thr Gly
                485                 490                 495

Val Gly Gln His Gln Met Trp Ala Ala Gln His Trp Thr Trp Arg Asn
            500                 505                 510
```

-continued

```
Pro His Thr Phe Ile Thr Ser Gly Gly Leu Gly Thr Met Gly Tyr Gly
        515                 520                 525

Leu Pro Ala Ala Ile Gly Ala Gln Val Ala Lys Pro Glu Ser Leu Val
    530                 535                 540

Ile Asp Ile Asp Gly Asp Ala Ser Phe Asn Met Thr Leu Thr Glu Leu
545                 550                 555                 560

Ser Ser Ala Val Gln Ala Gly Thr Pro Val Lys Ile Leu Ile Leu Asn
                565                 570                 575

Asn Glu Glu Gln Gly Met Val Thr Gln Trp Gln Ser Leu Phe Tyr Glu
            580                 585                 590

His Arg Tyr Ser His Thr His Gln Leu Asn Pro Asp Phe Ile Lys Leu
        595                 600                 605

Ala Glu Ala Met Gly Leu Lys Gly Leu Arg Val Lys Lys Gln Glu Glu
    610                 615                 620

Leu Asp Ala Lys Leu Lys Glu Phe Val Ser Thr Lys Gly Pro Val Leu
625                 630                 635                 640

Leu Glu Val Glu Val Asp Lys Lys Val Pro Val Leu Pro Met Val Ala
                645                 650                 655

Gly Gly Ser Gly Leu Asp Glu Phe Ile Asn Phe Asp Pro Glu Val Glu
            660                 665                 670

Arg Gln Gln Thr Glu Leu Arg His Lys Arg Thr Gly Gly Lys His
        675                 680                 685

<210> SEQ ID NO 17
<211> LENGTH: 1083
<212> TYPE: DNA
<213> ORGANISM: Saccharomyces cerevisiae
<220> FEATURE:
<221> NAME/KEY: CDS
<222> LOCATION: (1)..(1083)

<400> SEQUENCE: 17 atg tcg ata gtc tac aat aaa aca cca tta tta cgt caa ttc ttc ccc      48
Met Ser Ile Val Tyr Asn Lys Thr Pro Leu Leu Arg Gln Phe Phe Pro
1               5                   10                  15 gga aag gct tct gca caa ttt ttc ttg aaa tat gaa tgc ctt caa cca      96
Gly Lys Ala Ser Ala Gln Phe Phe Leu Lys Tyr Glu Cys Leu Gln Pro
                20                  25                  30 agt ggc tcc ttc aaa agt aga gga atc ggt aat ctc atc atg aaa agt     144
Ser Gly Ser Phe Lys Ser Arg Gly Ile Gly Asn Leu Ile Met Lys Ser
            35                  40                  45 gcc att cga att caa aag gac ggt aaa aga tct cct cag gtt ttc gct     192
Ala Ile Arg Ile Gln Lys Asp Gly Lys Arg Ser Pro Gln Val Phe Ala
        50                  55                  60 agt tct ggc ggt aat gcc ggt ttt gct gct gca aca gca tgt caa aga     240
Ser Ser Gly Gly Asn Ala Gly Phe Ala Ala Ala Thr Ala Cys Gln Arg
65                  70                  75                  80 ctg tct cta cca tgt aca gtc gtg gtt cct aca gcg aca aag aag aga     288
Leu Ser Leu Pro Cys Thr Val Val Val Pro Thr Ala Thr Lys Lys Arg
                85                  90                  95 atg gta gat aaa atc agg aac acc ggt gcc cag gtt atc gtg agt ggt     336
Met Val Asp Lys Ile Arg Asn Thr Gly Ala Gln Val Ile Val Ser Gly
                100                 105                 110 gcc tac tgg aaa gaa gca gat act ttt tta aaa aca aat gtc atg aat     384
Ala Tyr Trp Lys Glu Ala Asp Thr Phe Leu Lys Thr Asn Val Met Asn
            115                 120                 125 aaa ata gac tct cag gtc att gag ccc att tat gtt cat ccc ttc gat     432
Lys Ile Asp Ser Gln Val Ile Glu Pro Ile Tyr Val His Pro Phe Asp
        130                 135                 140
```

```
aat ccg gat att tgg gaa gga cat tca tct atg ata gat gaa ata gta    480
Asn Pro Asp Ile Trp Glu Gly His Ser Ser Met Ile Asp Glu Ile Val
145                 150                 155                 160 caa gat ttg aaa tcg caa cat att tcc gtg aat aag gtt aaa ggc ata    528
Gln Asp Leu Lys Ser Gln His Ile Ser Val Asn Lys Val Lys Gly Ile
            165                 170                 175 gta tgc agc gtt ggt gga ggt ggt tta tac aat ggt att att caa ggt    576
Val Cys Ser Val Gly Gly Gly Gly Leu Tyr Asn Gly Ile Ile Gln Gly
        180                 185                 190 ttg gaa agg tat ggt tta gct gat agg atc cct att gtg ggg gtg gaa    624
Leu Glu Arg Tyr Gly Leu Ala Asp Arg Ile Pro Ile Val Gly Val Glu
    195                 200                 205 acg aat gga tgt cat gtt ttc aat act tct ttg aaa ata ggc caa cca    672
Thr Asn Gly Cys His Val Phe Asn Thr Ser Leu Lys Ile Gly Gln Pro
210                 215                 220 gtt caa ttc aag aag ata aca agt att gct act tct cta gga acg gcc    720
Val Gln Phe Lys Lys Ile Thr Ser Ile Ala Thr Ser Leu Gly Thr Ala
225                 230                 235                 240 gtg atc tct aat caa act ttc gaa tac gct cgc aaa tac aac acc aga    768
Val Ile Ser Asn Gln Thr Phe Glu Tyr Ala Arg Lys Tyr Asn Thr Arg
                245                 250                 255 tcc gtt gta ata gag gac aaa gat gtt att gaa acc tgt ctt aaa tat    816
Ser Val Val Ile Glu Asp Lys Asp Val Ile Glu Thr Cys Leu Lys Tyr
            260                 265                 270 aca cat caa ttc aat atg gtg att gaa ccg gca tgt ggc gcc gca ttg    864
Thr His Gln Phe Asn Met Val Ile Glu Pro Ala Cys Gly Ala Ala Leu
        275                 280                 285 cat ttg ggt tac aac act aag atc cta gaa aat gca ctg ggc tca aaa    912
His Leu Gly Tyr Asn Thr Lys Ile Leu Glu Asn Ala Leu Gly Ser Lys
    290                 295                 300 tta gct gcg gat gac att gtg ata att att gct tgt ggc ggc tcc tct    960
Leu Ala Ala Asp Asp Ile Val Ile Ile Ile Ala Cys Gly Gly Ser Ser
305                 310                 315                 320 aat act ata aag gac ttg gaa gaa gcg ttg gat agc atg aga aaa aaa   1008
Asn Thr Ile Lys Asp Leu Glu Glu Ala Leu Asp Ser Met Arg Lys Lys
                325                 330                 335 gac act cct gta ata gaa gtc gct gac aat ttc ata ttt cca gaa aaa   1056
Asp Thr Pro Val Ile Glu Val Ala Asp Asn Phe Ile Phe Pro Glu Lys
            340                 345                 350 aat att gtg aat tta aaa agt gct tga                                1083
Asn Ile Val Asn Leu Lys Ser Ala
        355                 360

<210> SEQ ID NO 18
<211> LENGTH: 360
<212> TYPE: PRT
<213> ORGANISM: Saccharomyces cerevisiae

<400> SEQUENCE: 18

Met Ser Ile Val Tyr Asn Lys Thr Pro Leu Leu Arg Gln Phe Phe Pro
1               5                   10                  15

Gly Lys Ala Ser Ala Gln Phe Phe Leu Lys Tyr Glu Cys Leu Gln Pro
            20                  25                  30

Ser Gly Ser Phe Lys Ser Arg Gly Ile Gly Asn Leu Ile Met Lys Ser
        35                  40                  45

Ala Ile Arg Ile Gln Lys Asp Gly Lys Arg Ser Pro Gln Val Phe Ala
    50                  55                  60

Ser Ser Gly Gly Asn Ala Gly Phe Ala Ala Ala Thr Ala Cys Gln Arg
65                  70                  75                  80
```

```
Leu Ser Leu Pro Cys Thr Val Val Pro Thr Ala Thr Lys Lys Arg
             85                  90                  95

Met Val Asp Lys Ile Arg Asn Thr Gly Ala Gln Val Ile Val Ser Gly
            100                 105                 110

Ala Tyr Trp Lys Glu Ala Asp Thr Phe Leu Lys Thr Asn Val Met Asn
        115                 120                 125

Lys Ile Asp Ser Gln Val Ile Glu Pro Ile Tyr Val His Pro Phe Asp
    130                 135                 140

Asn Pro Asp Ile Trp Glu Gly His Ser Ser Met Ile Asp Glu Ile Val
145                 150                 155                 160

Gln Asp Leu Lys Ser Gln His Ile Ser Val Asn Lys Val Lys Gly Ile
                165                 170                 175

Val Cys Ser Val Gly Gly Gly Leu Tyr Asn Gly Ile Ile Gln Gly
            180                 185                 190

Leu Glu Arg Tyr Gly Leu Ala Asp Arg Ile Pro Ile Val Gly Val Glu
        195                 200                 205

Thr Asn Gly Cys His Val Phe Asn Thr Ser Leu Lys Ile Gly Gln Pro
    210                 215                 220

Val Gln Phe Lys Lys Ile Thr Ser Ile Ala Thr Ser Leu Gly Thr Ala
225                 230                 235                 240

Val Ile Ser Asn Gln Thr Phe Glu Tyr Ala Arg Lys Tyr Asn Thr Arg
                245                 250                 255

Ser Val Val Ile Glu Asp Lys Asp Val Ile Glu Thr Cys Leu Lys Tyr
            260                 265                 270

Thr His Gln Phe Asn Met Val Ile Glu Pro Ala Cys Gly Ala Ala Leu
        275                 280                 285

His Leu Gly Tyr Asn Thr Lys Ile Leu Glu Asn Ala Leu Gly Ser Lys
    290                 295                 300

Leu Ala Ala Asp Asp Ile Val Ile Ile Ala Cys Gly Gly Ser Ser
305                 310                 315                 320

Asn Thr Ile Lys Asp Leu Glu Glu Ala Leu Asp Ser Met Arg Lys Lys
                325                 330                 335

Asp Thr Pro Val Ile Glu Val Ala Asp Asn Phe Ile Phe Pro Glu Lys
            340                 345                 350

Asn Ile Val Asn Leu Lys Ser Ala
        355                 360

<210> SEQ ID NO 19
<211> LENGTH: 1731
<212> TYPE: DNA
<213> ORGANISM: Saccharomyces cerevisiae
<220> FEATURE:
<221> NAME/KEY: CDS
<222> LOCATION: (1)..(1731)

<400> SEQUENCE: 19 atg tca gct act cta cta aag caa cca tta tgt acg gtt gtt cgg caa     48
Met Ser Ala Thr Leu Leu Lys Gln Pro Leu Cys Thr Val Val Arg Gln
1               5                   10                  15 ggt aaa cag tcc aaa gtg tct gga ttg aac ctt ttg aga cta aag gct     96
Gly Lys Gln Ser Lys Val Ser Gly Leu Asn Leu Leu Arg Leu Lys Ala
            20                  25                  30 cat ttg cac aga caa cac ctg tca cct tcc ttg ata aaa cta cac tct    144
His Leu His Arg Gln His Leu Ser Pro Ser Leu Ile Lys Leu His Ser
        35                  40                  45
```

```
gaa ttg aaa ttg gat gag ctg caa act gat aac acc cct gat tac gtc      192
Glu Leu Lys Leu Asp Glu Leu Gln Thr Asp Asn Thr Pro Asp Tyr Val
     50              55                  60 cgt tta gtt tta agg tcc tct gta tac gat gtt att aat gaa tct cca      240
Arg Leu Val Leu Arg Ser Ser Val Tyr Asp Val Ile Asn Glu Ser Pro
 65              70                  75                  80 atc tct caa ggt gta ggt ttg tct tcc cgt cta aac acg aat gtc atc      288
Ile Ser Gln Gly Val Gly Leu Ser Ser Arg Leu Asn Thr Asn Val Ile
                 85                  90                  95 ttg aaa aga gaa gat cta ttg cct gtt ttc tct ttc aag ctt cgt ggt      336
Leu Lys Arg Glu Asp Leu Leu Pro Val Phe Ser Phe Lys Leu Arg Gly
             100                 105                 110 gcc tat aac atg att gcc aag ttg gac gat tct caa aga aac cag ggt      384
Ala Tyr Asn Met Ile Ala Lys Leu Asp Asp Ser Gln Arg Asn Gln Gly
         115                 120                 125 gtt att gcc tgt tca gct ggg aat cat gcc caa ggt gtg gcc ttt gct      432
Val Ile Ala Cys Ser Ala Gly Asn His Ala Gln Gly Val Ala Phe Ala
     130                 135                 140 gct aaa cac ttg aaa ata cct gct act atc gtt atg cct gtt tgt aca      480
Ala Lys His Leu Lys Ile Pro Ala Thr Ile Val Met Pro Val Cys Thr
145                 150                 155                 160 cca tct att aag tat caa aat gtc tcg aga tta ggg tct caa gtc gtc      528
Pro Ser Ile Lys Tyr Gln Asn Val Ser Arg Leu Gly Ser Gln Val Val
                165                 170                 175 cta tat ggt aac gat ttt gac gag gct aag gct gaa tgt gcc aaa ttg      576
Leu Tyr Gly Asn Asp Phe Asp Glu Ala Lys Ala Glu Cys Ala Lys Leu
            180                 185                 190 gct gaa gag cgt ggc ttg acg aac att cct cct ttc gat cat cct tat      624
Ala Glu Glu Arg Gly Leu Thr Asn Ile Pro Pro Phe Asp His Pro Tyr
        195                 200                 205 gtc att gcc ggt caa ggt act gta gct atg gaa atc cta aga caa gta      672
Val Ile Ala Gly Gln Gly Thr Val Ala Met Glu Ile Leu Arg Gln Val
    210                 215                 220 cgt acc gct aat aag atc ggt gct gtc ttt gtt ccc gtc ggc ggt ggt      720
Arg Thr Ala Asn Lys Ile Gly Ala Val Phe Val Pro Val Gly Gly Gly
225                 230                 235                 240 ggt tta att gct ggt att ggt gct tat ttg aaa agg gtt gct cct cat      768
Gly Leu Ile Ala Gly Ile Gly Ala Tyr Leu Lys Arg Val Ala Pro His
                245                 250                 255 atc aaa atc att ggt gtt gaa act tac gat gcg gcc act tta cat aat      816
Ile Lys Ile Ile Gly Val Glu Thr Tyr Asp Ala Ala Thr Leu His Asn
            260                 265                 270 tcc ttg caa cgc aac cag aga act cct tta cct gtg gtg ggt act ttt      864
Ser Leu Gln Arg Asn Gln Arg Thr Pro Leu Pro Val Val Gly Thr Phe
        275                 280                 285 gcc gat ggt acg tct gtg cgt atg att ggt gaa gaa aca ttt aga gtc      912
Ala Asp Gly Thr Ser Val Arg Met Ile Gly Glu Glu Thr Phe Arg Val
    290                 295                 300 gcc caa caa gtg gtt gat gaa gtt gtt ctt gtt aac act gac gaa atc      960
Ala Gln Gln Val Val Asp Glu Val Val Leu Val Asn Thr Asp Glu Ile
305                 310                 315                 320 tgt gct gca gta aag gat att ttt gaa gat act aga agt att gta gaa     1008
Cys Ala Ala Val Lys Asp Ile Phe Glu Asp Thr Arg Ser Ile Val Glu
                325                 330                 335 cca tct ggt gcc ctt tca gta gcc ggt atg aag aaa tac atc tct acc     1056
Pro Ser Gly Ala Leu Ser Val Ala Gly Met Lys Lys Tyr Ile Ser Thr
            340                 345                 350 gta cat cca gaa att gac cac act aaa aac acc tat gtt ccc atc ctt     1104
Val His Pro Glu Ile Asp His Thr Lys Asn Thr Tyr Val Pro Ile Leu
        355                 360                 365
```

| | | |
|---|---|---|
| tct ggt gct aac atg aac ttt gat aga tta aga ttt gtt tcc gaa cgt<br>Ser Gly Ala Asn Met Asn Phe Asp Arg Leu Arg Phe Val Ser Glu Arg<br>370 375 380 | | 1152 |
| gct gtt ctt ggt gaa gga aag gaa gtc ttc atg tta gtt act tta ccc<br>Ala Val Leu Gly Glu Gly Lys Glu Val Phe Met Leu Val Thr Leu Pro<br>385 390 395 400 | | 1200 |
| gac gtc cct ggt gcg ttc aag aaa atg caa aag atc atc cac cca aga<br>Asp Val Pro Gly Ala Phe Lys Lys Met Gln Lys Ile Ile His Pro Arg<br>405 410 415 | | 1248 |
| tct gtc act gaa ttc tct tac cgt tac aat gaa cat cgt cat gag tcc<br>Ser Val Thr Glu Phe Ser Tyr Arg Tyr Asn Glu His Arg His Glu Ser<br>420 425 430 | | 1296 |
| tct agt gaa gtg ccc aag gct tac att tac act tct ttc agc gtc gtt<br>Ser Ser Glu Val Pro Lys Ala Tyr Ile Tyr Thr Ser Phe Ser Val Val<br>435 440 445 | | 1344 |
| gac aga gaa aag gaa atc aag caa gtt atg caa cag ttg aat gct tta<br>Asp Arg Glu Lys Glu Ile Lys Gln Val Met Gln Gln Leu Asn Ala Leu<br>450 455 460 | | 1392 |
| ggt ttt gaa gct gtg gat atc tcc gat aac gaa ttg gct aaa tct cat<br>Gly Phe Glu Ala Val Asp Ile Ser Asp Asn Glu Leu Ala Lys Ser His<br>465 470 475 480 | | 1440 |
| ggt aga tac ttg gtt ggt ggt gct tct aag gtt cct aat gaa aga att<br>Gly Arg Tyr Leu Val Gly Gly Ala Ser Lys Val Pro Asn Glu Arg Ile<br>485 490 495 | | 1488 |
| att tca ttt gaa ttc cct gaa aga cca ggt gcc ttg act agg ttc ctt<br>Ile Ser Phe Glu Phe Pro Glu Arg Pro Gly Ala Leu Thr Arg Phe Leu<br>500 505 510 | | 1536 |
| gga ggc cta agc gat tct tgg aat ctt act tta ttc cat tat aga aac<br>Gly Gly Leu Ser Asp Ser Trp Asn Leu Thr Leu Phe His Tyr Arg Asn<br>515 520 525 | | 1584 |
| cat ggt gcc gat atc ggt aag gtt tta gct ggt att tcc gtt cct cca<br>His Gly Ala Asp Ile Gly Lys Val Leu Ala Gly Ile Ser Val Pro Pro<br>530 535 540 | | 1632 |
| agg gaa aac tta acc ttc caa aaa ttc ttg gaa gat tta ggc tac act<br>Arg Glu Asn Leu Thr Phe Gln Lys Phe Leu Glu Asp Leu Gly Tyr Thr<br>545 550 555 560 | | 1680 |
| tat cat gat gaa act gat aac act gtt tat caa aaa ttc ttg aaa tat<br>Tyr His Asp Glu Thr Asp Asn Thr Val Tyr Gln Lys Phe Leu Lys Tyr<br>565 570 575 | | 1728 |
| taa | | 1731 |

<210> SEQ ID NO 20
<211> LENGTH: 576
<212> TYPE: PRT
<213> ORGANISM: Saccharomyces cerevisiae

<400> SEQUENCE: 20

Met Ser Ala Thr Leu Leu Lys Gln Pro Leu Cys Thr Val Val Arg Gln
1               5                   10                  15

Gly Lys Gln Ser Lys Val Ser Gly Leu Asn Leu Leu Arg Leu Lys Ala
            20                  25                  30

His Leu His Arg Gln His Leu Ser Pro Ser Leu Ile Lys Leu His Ser
        35                  40                  45

Glu Leu Lys Leu Asp Glu Leu Gln Thr Asp Asn Thr Pro Asp Tyr Val
    50                  55                  60

Arg Leu Val Leu Arg Ser Ser Val Tyr Asp Val Ile Asn Glu Ser Pro
65                  70                  75                  80

Ile Ser Gln Gly Val Gly Leu Ser Ser Arg Leu Asn Thr Asn Val Ile
                85                  90                  95

```
Leu Lys Arg Glu Asp Leu Leu Pro Val Phe Ser Phe Lys Leu Arg Gly
            100                 105                 110

Ala Tyr Asn Met Ile Ala Lys Leu Asp Asp Ser Gln Arg Asn Gln Gly
        115                 120                 125

Val Ile Ala Cys Ser Ala Gly Asn His Ala Gln Gly Val Ala Phe Ala
    130                 135                 140

Ala Lys His Leu Lys Ile Pro Ala Thr Ile Val Met Pro Val Cys Thr
145                 150                 155                 160

Pro Ser Ile Lys Tyr Gln Asn Val Ser Arg Leu Gly Ser Gln Val Val
                165                 170                 175

Leu Tyr Gly Asn Asp Phe Asp Glu Ala Lys Ala Glu Cys Ala Lys Leu
            180                 185                 190

Ala Glu Glu Arg Gly Leu Thr Asn Ile Pro Pro Phe Asp His Pro Tyr
        195                 200                 205

Val Ile Ala Gly Gln Gly Thr Val Ala Met Glu Ile Leu Arg Gln Val
    210                 215                 220

Arg Thr Ala Asn Lys Ile Gly Ala Val Phe Val Pro Val Gly Gly Gly
225                 230                 235                 240

Gly Leu Ile Ala Gly Ile Gly Ala Tyr Leu Lys Arg Val Ala Pro His
                245                 250                 255

Ile Lys Ile Ile Gly Val Glu Thr Tyr Asp Ala Ala Thr Leu His Asn
            260                 265                 270

Ser Leu Gln Arg Asn Gln Arg Thr Pro Leu Pro Val Val Gly Thr Phe
        275                 280                 285

Ala Asp Gly Thr Ser Val Arg Met Ile Gly Glu Glu Thr Phe Arg Val
    290                 295                 300

Ala Gln Gln Val Val Asp Glu Val Val Leu Val Asn Thr Asp Glu Ile
305                 310                 315                 320

Cys Ala Ala Val Lys Asp Ile Phe Glu Asp Thr Arg Ser Ile Val Glu
                325                 330                 335

Pro Ser Gly Ala Leu Ser Val Ala Gly Met Lys Lys Tyr Ile Ser Thr
            340                 345                 350

Val His Pro Glu Ile Asp His Thr Lys Asn Thr Tyr Val Pro Ile Leu
        355                 360                 365

Ser Gly Ala Asn Met Asn Phe Asp Arg Leu Arg Phe Val Ser Glu Arg
    370                 375                 380

Ala Val Leu Gly Glu Gly Lys Glu Val Phe Met Leu Val Thr Leu Pro
385                 390                 395                 400

Asp Val Pro Gly Ala Phe Lys Lys Met Gln Lys Ile Ile His Pro Arg
                405                 410                 415

Ser Val Thr Glu Phe Ser Tyr Arg Tyr Asn Glu His Arg His Glu Ser
            420                 425                 430

Ser Ser Glu Val Pro Lys Ala Tyr Ile Tyr Thr Ser Phe Ser Val Val
        435                 440                 445

Asp Arg Glu Lys Glu Ile Lys Gln Val Met Gln Gln Leu Asn Ala Leu
    450                 455                 460

Gly Phe Glu Ala Val Asp Ile Ser Asp Asn Glu Leu Ala Lys Ser His
465                 470                 475                 480

Gly Arg Tyr Leu Val Gly Gly Ala Ser Lys Val Pro Asn Glu Arg Ile
                485                 490                 495

Ile Ser Phe Glu Phe Pro Glu Arg Pro Gly Ala Leu Thr Arg Phe Leu
            500                 505                 510
```

```
Gly Gly Leu Ser Asp Ser Trp Asn Leu Thr Leu Phe His Tyr Arg Asn
            515                 520                 525

His Gly Ala Asp Ile Gly Lys Val Leu Ala Gly Ile Ser Val Pro Pro
    530                 535                 540

Arg Glu Asn Leu Thr Phe Gln Lys Phe Leu Glu Asp Leu Gly Tyr Thr
545                 550                 555                 560

Tyr His Asp Glu Thr Asp Asn Thr Val Tyr Gln Lys Phe Leu Lys Tyr
                565                 570                 575

<210> SEQ ID NO 21
<211> LENGTH: 1182
<212> TYPE: DNA
<213> ORGANISM: Saccharomyces cerevisiae
<220> FEATURE:
<221> NAME/KEY: CDS
<222> LOCATION: (1)..(1182)

<400> SEQUENCE: 21
```

| | | | | | | | | | | | | | | | | |
|---|---|---|---|---|---|---|---|---|---|---|---|---|---|---|---|---|
| atg | ttg | cag | aga | cat | tcc | ttg | aag | ttg | ggg | aaa | ttc | tcc | atc | aga | aca | 48 |
| Met | Leu | Gln | Arg | His | Ser | Leu | Lys | Leu | Gly | Lys | Phe | Ser | Ile | Arg | Thr | |
| 1 | | | | 5 | | | | | 10 | | | | | 15 | | |
| ctc | gct | act | ggt | gcc | cca | tta | gat | gca | tcc | aaa | cta | aaa | att | act | aga | 96 |
| Leu | Ala | Thr | Gly | Ala | Pro | Leu | Asp | Ala | Ser | Lys | Leu | Lys | Ile | Thr | Arg | |
| | | | 20 | | | | | 25 | | | | | 30 | | | |
| aac | cca | aat | cca | tcc | aag | cca | aga | cca | aat | gaa | gaa | tta | gtg | ttc | ggc | 144 |
| Asn | Pro | Asn | Pro | Ser | Lys | Pro | Arg | Pro | Asn | Glu | Glu | Leu | Val | Phe | Gly | |
| | | 35 | | | | | 40 | | | | | 45 | | | | |
| cag | aca | ttc | acc | gat | cat | atg | ttg | acc | att | cct | tgg | tca | gcc | aaa | gaa | 192 |
| Gln | Thr | Phe | Thr | Asp | His | Met | Leu | Thr | Ile | Pro | Trp | Ser | Ala | Lys | Glu | |
| | 50 | | | | | 55 | | | | | 60 | | | | | |
| ggg | tgg | ggc | act | cca | cac | atc | aag | cct | tac | ggt | aat | ctt | tct | ctt | gac | 240 |
| Gly | Trp | Gly | Thr | Pro | His | Ile | Lys | Pro | Tyr | Gly | Asn | Leu | Ser | Leu | Asp | |
| 65 | | | | | 70 | | | | | 75 | | | | | 80 | |
| cca | tct | gct | tgt | gta | ttc | cat | tat | gca | ttt | gaa | tta | ttt | gaa | ggt | ttg | 288 |
| Pro | Ser | Ala | Cys | Val | Phe | His | Tyr | Ala | Phe | Glu | Leu | Phe | Glu | Gly | Leu | |
| | | | | 85 | | | | | 90 | | | | | 95 | | |
| aaa | gcc | tac | aga | act | cct | caa | aat | act | atc | acc | atg | ttc | cgt | ccg | gat | 336 |
| Lys | Ala | Tyr | Arg | Thr | Pro | Gln | Asn | Thr | Ile | Thr | Met | Phe | Arg | Pro | Asp | |
| | | | 100 | | | | | 105 | | | | | 110 | | | |
| aag | aac | atg | gcc | cgt | atg | aac | aag | tct | gcc | gct | aga | att | tgt | ttg | cca | 384 |
| Lys | Asn | Met | Ala | Arg | Met | Asn | Lys | Ser | Ala | Ala | Arg | Ile | Cys | Leu | Pro | |
| | | 115 | | | | | 120 | | | | | 125 | | | | |
| act | ttc | gaa | tct | gaa | gaa | ttg | atc | aaa | ctt | acc | ggg | aaa | ttg | atc | gaa | 432 |
| Thr | Phe | Glu | Ser | Glu | Glu | Leu | Ile | Lys | Leu | Thr | Gly | Lys | Leu | Ile | Glu | |
| | 130 | | | | | 135 | | | | | 140 | | | | | |
| caa | gat | aaa | cac | ttg | gtt | cct | caa | ggt | aat | ggt | tac | tca | tta | tac | atc | 480 |
| Gln | Asp | Lys | His | Leu | Val | Pro | Gln | Gly | Asn | Gly | Tyr | Ser | Leu | Tyr | Ile | |
| 145 | | | | | 150 | | | | | 155 | | | | | 160 | |
| aga | cca | aca | atg | att | ggt | aca | tcc | aag | ggt | tta | ggt | gtt | ggc | act | ccc | 528 |
| Arg | Pro | Thr | Met | Ile | Gly | Thr | Ser | Lys | Gly | Leu | Gly | Val | Gly | Thr | Pro | |
| | | | | 165 | | | | | 170 | | | | | 175 | | |
| tcc | gag | gct | ctt | ctt | tat | gtt | att | act | tct | cca | gtc | ggt | cct | tat | tat | 576 |
| Ser | Glu | Ala | Leu | Leu | Tyr | Val | Ile | Thr | Ser | Pro | Val | Gly | Pro | Tyr | Tyr | |
| | | | 180 | | | | | 185 | | | | | 190 | | | |
| aag | act | ggt | ttc | aaa | gcc | gta | cgt | ctt | gaa | gca | aca | gac | tat | gct | aca | 624 |
| Lys | Thr | Gly | Phe | Lys | Ala | Val | Arg | Leu | Glu | Ala | Thr | Asp | Tyr | Ala | Thr | |
| | | 195 | | | | | 200 | | | | | 205 | | | | |
| aga | gct | tgg | cca | ggt | ggt | gtt | ggc | gac | aaa | aaa | ttg | ggt | gct | aac | tat | 672 |
| Arg | Ala | Trp | Pro | Gly | Gly | Val | Gly | Asp | Lys | Lys | Leu | Gly | Ala | Asn | Tyr | |
| | 210 | | | | | 215 | | | | | 220 | | | | | |

```
gcc cca tgc atc tta cct caa cta caa gct gcc aaa aga ggg tac caa    720
Ala Pro Cys Ile Leu Pro Gln Leu Gln Ala Ala Lys Arg Gly Tyr Gln
225                 230                 235                 240 caa aat cta tgg ttg ttc ggc cca gaa aag aac atc act gag gtt ggt    768
Gln Asn Leu Trp Leu Phe Gly Pro Glu Lys Asn Ile Thr Glu Val Gly
            245                 250                 255 act atg aac gtg ttc ttc gtt ttc ctc aac aaa gtc act ggc aag aag    816
Thr Met Asn Val Phe Phe Val Phe Leu Asn Lys Val Thr Gly Lys Lys
        260                 265                 270 gaa ttg gtt acc gct cca tta gat ggt acc att tta gaa ggt gtt acc    864
Glu Leu Val Thr Ala Pro Leu Asp Gly Thr Ile Leu Glu Gly Val Thr
    275                 280                 285 aga gac tct gtt tta aca ttg gct cgt gac aaa cta gat cct caa gaa    912
Arg Asp Ser Val Leu Thr Leu Ala Arg Asp Lys Leu Asp Pro Gln Glu
290                 295                 300 tgg gac atc aac gag cgt tat tac act att act gaa gtc gcc act aga    960
Trp Asp Ile Asn Glu Arg Tyr Tyr Thr Ile Thr Glu Val Ala Thr Arg
305                 310                 315                 320 gca aaa caa ggt gaa cta tta gaa gcc ttc ggt tct ggt act gct gct   1008
Ala Lys Gln Gly Glu Leu Leu Glu Ala Phe Gly Ser Gly Thr Ala Ala
            325                 330                 335 gtc gtt tca cct atc aag gaa att ggc tgg aac aac gaa gat att cat   1056
Val Val Ser Pro Ile Lys Glu Ile Gly Trp Asn Asn Glu Asp Ile His
        340                 345                 350 gtt cca cta ttg cct ggt gaa caa tgt ggt gca ttg acc aag caa gtt   1104
Val Pro Leu Leu Pro Gly Glu Gln Cys Gly Ala Leu Thr Lys Gln Val
    355                 360                 365 gct caa tgg att gct gat atc caa tac ggt aga gtc aat tat ggt aac   1152
Ala Gln Trp Ile Ala Asp Ile Gln Tyr Gly Arg Val Asn Tyr Gly Asn
370                 375                 380 tgg tca aaa act gtt gcc gac ttg aac taa                           1182
Trp Ser Lys Thr Val Ala Asp Leu Asn
385                 390

<210> SEQ ID NO 22
<211> LENGTH: 393
<212> TYPE: PRT
<213> ORGANISM: Saccharomyces cerevisiae

<400> SEQUENCE: 22

Met Leu Gln Arg His Ser Leu Lys Leu Gly Lys Phe Ser Ile Arg Thr
1               5                   10                  15

Leu Ala Thr Gly Ala Pro Leu Asp Ala Ser Lys Leu Lys Ile Thr Arg
            20                  25                  30

Asn Pro Asn Pro Ser Lys Pro Arg Pro Asn Glu Glu Leu Val Phe Gly
        35                  40                  45

Gln Thr Phe Thr Asp His Met Leu Thr Ile Pro Trp Ser Ala Lys Glu
    50                  55                  60

Gly Trp Gly Thr Pro His Ile Lys Pro Tyr Gly Asn Leu Ser Leu Asp
65                  70                  75                  80

Pro Ser Ala Cys Val Phe His Tyr Ala Phe Glu Leu Phe Glu Gly Leu
                85                  90                  95

Lys Ala Tyr Arg Thr Pro Gln Asn Thr Ile Thr Met Phe Arg Pro Asp
            100                 105                 110

Lys Asn Met Ala Arg Met Asn Lys Ser Ala Ala Arg Ile Cys Leu Pro
        115                 120                 125

Thr Phe Glu Ser Glu Glu Leu Ile Lys Leu Thr Gly Lys Leu Ile Glu
    130                 135                 140
```

```
Gln Asp Lys His Leu Val Pro Gln Gly Asn Gly Tyr Ser Leu Tyr Ile
145                 150                 155                 160

Arg Pro Thr Met Ile Gly Thr Ser Lys Gly Leu Gly Val Gly Thr Pro
                165                 170                 175

Ser Glu Ala Leu Leu Tyr Val Ile Thr Ser Pro Val Gly Pro Tyr Tyr
            180                 185                 190

Lys Thr Gly Phe Lys Ala Val Arg Leu Glu Ala Thr Asp Tyr Ala Thr
        195                 200                 205

Arg Ala Trp Pro Gly Val Gly Asp Lys Lys Leu Gly Ala Asn Tyr
    210                 215                 220

Ala Pro Cys Ile Leu Pro Gln Leu Gln Ala Ala Lys Arg Gly Tyr Gln
225                 230                 235                 240

Gln Asn Leu Trp Leu Phe Gly Pro Glu Lys Asn Ile Thr Glu Val Gly
                245                 250                 255

Thr Met Asn Val Phe Phe Val Phe Leu Asn Lys Val Thr Gly Lys Lys
            260                 265                 270

Glu Leu Val Thr Ala Pro Leu Asp Gly Thr Ile Leu Glu Gly Val Thr
        275                 280                 285

Arg Asp Ser Val Leu Thr Leu Ala Arg Asp Lys Leu Asp Pro Gln Glu
    290                 295                 300

Trp Asp Ile Asn Glu Arg Tyr Tyr Thr Ile Thr Glu Val Ala Thr Arg
305                 310                 315                 320

Ala Lys Gln Gly Glu Leu Leu Glu Ala Phe Gly Ser Gly Thr Ala Ala
                325                 330                 335

Val Val Ser Pro Ile Lys Glu Ile Gly Trp Asn Asn Glu Asp Ile His
            340                 345                 350

Val Pro Leu Leu Pro Gly Glu Gln Cys Gly Ala Leu Thr Lys Gln Val
        355                 360                 365

Ala Gln Trp Ile Ala Asp Ile Gln Tyr Gly Arg Val Asn Tyr Gly Asn
    370                 375                 380

Trp Ser Lys Thr Val Ala Asp Leu Asn
385                 390

<210> SEQ ID NO 23
<211> LENGTH: 2037
<212> TYPE: DNA
<213> ORGANISM: Saccharomyces cerevisiae
<220> FEATURE:
<221> NAME/KEY: CDS
<222> LOCATION: (1)..(2037)

<400> SEQUENCE: 23 atg gga ctc tta gct ttg ggc acg cct ttg cag tgg ttt gag tct agg    48
Met Gly Leu Leu Ala Leu Gly Thr Pro Leu Gln Trp Phe Glu Ser Arg
1               5                   10                  15 acg tac aat gaa cac ata agg gat gaa ggt atc gag cag ttg ttg tat    96
Thr Tyr Asn Glu His Ile Arg Asp Glu Gly Ile Glu Gln Leu Leu Tyr
            20                  25                  30 att ttc caa gct gct ggt aaa aga gac aat gac cct ctt ttt tgg gga   144
Ile Phe Gln Ala Ala Gly Lys Arg Asp Asn Asp Pro Leu Phe Trp Gly
        35                  40                  45 gac gag ctt gag tac atg gtt gta gat ttt gat gat aag gag aga aat   192
Asp Glu Leu Glu Tyr Met Val Val Asp Phe Asp Asp Lys Glu Arg Asn
    50                  55                  60 tct atg ctc gac gtt tgc cat gac aag ata ctc act gag ctt aat atg   240
Ser Met Leu Asp Val Cys His Asp Lys Ile Leu Thr Glu Leu Asn Met
65                  70                  75                  80
```

-continued

| | | |
|---|---|---|
| gag gat tcg tcc ctt tgt gag gct aac gat gtg agt ttt cac cct gag<br>Glu Asp Ser Ser Leu Cys Glu Ala Asn Asp Val Ser Phe His Pro Glu<br>              85                        90                        95 | 288 |
| tat ggc cgg tat atg tta gag gca aca cca gct tct cca tat ttg aat<br>Tyr Gly Arg Tyr Met Leu Glu Ala Thr Pro Ala Ser Pro Tyr Leu Asn<br>              100                     105                   110 | 336 |
| tac gtg ggt agt tac gtt gag gtt aac atg caa aaa aga cgt gcc att<br>Tyr Val Gly Ser Tyr Val Glu Val Asn Met Gln Lys Arg Arg Ala Ile<br>              115                     120                   125 | 384 |
| gca gaa tat aag cta tct gaa tat gcg aga caa gat agt aaa aat aac<br>Ala Glu Tyr Lys Leu Ser Glu Tyr Ala Arg Gln Asp Ser Lys Asn Asn<br>130                        135                     140 | 432 |
| ttg cat gtg ggc tcc agg tct gtc cct ttg acg ctg act gtc ttc ccg<br>Leu His Val Gly Ser Arg Ser Val Pro Leu Thr Leu Thr Val Phe Pro<br>145                        150                     155                   160 | 480 |
| agg atg gga tgc ccc gac ttt att aac att aag gat ccg tgg aat cat<br>Arg Met Gly Cys Pro Asp Phe Ile Asn Ile Lys Asp Pro Trp Asn His<br>                   165                     170                   175 | 528 |
| aaa aat gcc gct tcc agg tct ctg ttt tta ccc gat gaa gtc att aac<br>Lys Asn Ala Ala Ser Arg Ser Leu Phe Leu Pro Asp Glu Val Ile Asn<br>             180                     185                   190 | 576 |
| aga cat gtc agg ttt cct aac ttg aca gca tcc atc agg acc agg cgt<br>Arg His Val Arg Phe Pro Asn Leu Thr Ala Ser Ile Arg Thr Arg Arg<br>             195                     200                   205 | 624 |
| ggt gaa aaa gtt tgc atg aat gtt ccc atg tat aaa gat ata gct act<br>Gly Glu Lys Val Cys Met Asn Val Pro Met Tyr Lys Asp Ile Ala Thr<br>210                       215                     220 | 672 |
| cca gaa acg gat gac tcc atc tac gat cga gat tgg ttt tta cca gaa<br>Pro Glu Thr Asp Asp Ser Ile Tyr Asp Arg Asp Trp Phe Leu Pro Glu<br>225                        230                     235                   240 | 720 |
| gac aaa gag gcg aaa ctg gct tcc aaa ccg ggt ttc att tat atg gat<br>Asp Lys Glu Ala Lys Leu Ala Ser Lys Pro Gly Phe Ile Tyr Met Asp<br>                     245                     250                   255 | 768 |
| tcc atg ggt ttt ggc atg ggc tgt tcg tgc tta caa gtg acc ttt cag<br>Ser Met Gly Phe Gly Met Gly Cys Ser Cys Leu Gln Val Thr Phe Gln<br>             260                     265                   270 | 816 |
| gca ccc aat atc aac aag gca cgt tac ctg tac gat gca tta gtg aat<br>Ala Pro Asn Ile Asn Lys Ala Arg Tyr Leu Tyr Asp Ala Leu Val Asn<br>             275                     280                   285 | 864 |
| ttt gca cct ata atg cta gcc ttc tct gcc gct gcg cct gct ttt aaa<br>Phe Ala Pro Ile Met Leu Ala Phe Ser Ala Ala Ala Pro Ala Phe Lys<br>             290                     295                   300 | 912 |
| ggt tgg cta gcc gac caa gat gtt cgt tgg aat gtg ata tct ggt gcg<br>Gly Trp Leu Ala Asp Gln Asp Val Arg Trp Asn Val Ile Ser Gly Ala<br>305                        310                     315                   320 | 960 |
| gtg gac gac cgt act ccg aag gaa aga ggt gtt gcg cca tta cta ccc<br>Val Asp Asp Arg Thr Pro Lys Glu Arg Gly Val Ala Pro Leu Leu Pro<br>                   325                     330                   335 | 1008 |
| aaa tac aac aag aac gga ttt gga ggc att gcc aaa gac gta caa gat<br>Lys Tyr Asn Lys Asn Gly Phe Gly Gly Ile Ala Lys Asp Val Gln Asp<br>                   340                     345                   350 | 1056 |
| aaa gtc ctt gaa ata cca aag tca aga tat agt tcg gtt gat ctt ttc<br>Lys Val Leu Glu Ile Pro Lys Ser Arg Tyr Ser Ser Val Asp Leu Phe<br>             355                     360                   365 | 1104 |
| ttg ggt ggg tcg aaa ttt ttc aat agg act tat aac gac aca aat gta<br>Leu Gly Gly Ser Lys Phe Phe Asn Arg Thr Tyr Asn Asp Thr Asn Val<br>370                        375                     380 | 1152 |
| cct att aat gaa aaa gta tta gga cga cta cta gag aat gat aag gcg<br>Pro Ile Asn Glu Lys Val Leu Gly Arg Leu Leu Glu Asn Asp Lys Ala<br>385                        390                     395                   400 | 1200 |

-continued

| | | |
|---|---|---|
| cca ctg gac tat gat ctt gct aaa cat ttt gcg cat ctc tac ata aga<br>Pro Leu Asp Tyr Asp Leu Ala Lys His Phe Ala His Leu Tyr Ile Arg<br>405 410 415 | | 1248 |
| gat cca gta tct aca ttc gaa gaa ctg ttg aat cag gac aac aaa acg<br>Asp Pro Val Ser Thr Phe Glu Glu Leu Leu Asn Gln Asp Asn Lys Thr<br>420 425 430 | | 1296 |
| tct tca aat cac ttt gaa aac atc caa agt aca aat tgg cag aca tta<br>Ser Ser Asn His Phe Glu Asn Ile Gln Ser Thr Asn Trp Gln Thr Leu<br>435 440 445 | | 1344 |
| cgt ttt aaa ccc cca caa caa gca acc ccg gac aaa aag gat tct<br>Arg Phe Lys Pro Pro Thr Gln Gln Ala Thr Pro Asp Lys Lys Asp Ser<br>450 455 460 | | 1392 |
| cct ggt tgg aga gtg gaa ttc aga cca ttt gaa gtg caa cta tta gat<br>Pro Gly Trp Arg Val Glu Phe Arg Pro Phe Glu Val Gln Leu Leu Asp<br>465 470 475 480 | | 1440 |
| ttt gag aac gct gcg tat tcc gtg ctc ata tac ttg att gtc gat agc<br>Phe Glu Asn Ala Ala Tyr Ser Val Leu Ile Tyr Leu Ile Val Asp Ser<br>485 490 495 | | 1488 |
| att ttg acc ttt tcc gat aat att aac gca tat att cat atg tcc aaa<br>Ile Leu Thr Phe Ser Asp Asn Ile Asn Ala Tyr Ile His Met Ser Lys<br>500 505 510 | | 1536 |
| gta tgg gaa aat atg aag ata gcc cat cac aga gat gct atc cta ttt<br>Val Trp Glu Asn Met Lys Ile Ala His His Arg Asp Ala Ile Leu Phe<br>515 520 525 | | 1584 |
| gaa aaa ttt cat tgg aaa aaa tca ttt cgc aac gac acc gat gtg gaa<br>Glu Lys Phe His Trp Lys Lys Ser Phe Arg Asn Asp Thr Asp Val Glu<br>530 535 540 | | 1632 |
| act gaa gat tat tct ata agc gag att ttc cat aat cca gag aat ggt<br>Thr Glu Asp Tyr Ser Ile Ser Glu Ile Phe His Asn Pro Glu Asn Gly<br>545 550 555 560 | | 1680 |
| ata ttt cct caa ttt gtt acg cca atc cta tgc caa aaa ggg ttt gta<br>Ile Phe Pro Gln Phe Val Thr Pro Ile Leu Cys Gln Lys Gly Phe Val<br>565 570 575 | | 1728 |
| acc aaa gat tgg aaa gaa tta aag cat tct tcc aaa cac gag aga cta<br>Thr Lys Asp Trp Lys Glu Leu Lys His Ser Ser Lys His Glu Arg Leu<br>580 585 590 | | 1776 |
| tac tat tat tta aag cta att tct gat aga gca agc ggt gaa ttg cca<br>Tyr Tyr Tyr Leu Lys Leu Ile Ser Asp Arg Ala Ser Gly Glu Leu Pro<br>595 600 605 | | 1824 |
| aca aca gca aaa ttc ttt aga aat ttt gta cta caa cat cca gat tac<br>Thr Thr Ala Lys Phe Phe Arg Asn Phe Val Leu Gln His Pro Asp Tyr<br>610 615 620 | | 1872 |
| aaa cat gat tca aaa att tca aag tcg atc aat tat gat ttg ctt tct<br>Lys His Asp Ser Lys Ile Ser Lys Ser Ile Asn Tyr Asp Leu Leu Ser<br>625 630 635 640 | | 1920 |
| acg tgt gat aga ctt acc cat tta gac gat tca aaa ggt gaa ttg aca<br>Thr Cys Asp Arg Leu Thr His Leu Asp Asp Ser Lys Gly Glu Leu Thr<br>645 650 655 | | 1968 |
| tcc ttt tta gga gct gaa att gca gaa tat gta aaa aaa aat aag cct<br>Ser Phe Leu Gly Ala Glu Ile Ala Glu Tyr Val Lys Lys Asn Lys Pro<br>660 665 670 | | 2016 |
| tca ata gaa agc aaa tgt taa<br>Ser Ile Glu Ser Lys Cys<br>675 | | 2037 |

<210> SEQ ID NO 24
<211> LENGTH: 678
<212> TYPE: PRT
<213> ORGANISM: Saccharomyces cerevisiae

```
<400> SEQUENCE: 24

Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175

Lys Asn Ala Ala Ser Arg Ser Leu Phe Leu Pro Asp Glu Val Ile Asn
            180                 185                 190

Arg His Val Arg Phe Pro Asn Leu Thr Ala Ser Ile Arg Thr Arg Arg
        195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
                245                 250                 255

Ser Met Gly Phe Gly Met Gly Cys Ser Cys Leu Gln Val Thr Phe Gln
            260                 265                 270

Ala Pro Asn Ile Asn Lys Ala Arg Tyr Leu Tyr Asp Ala Leu Val Asn
        275                 280                 285

Phe Ala Pro Ile Met Leu Ala Phe Ser Ala Ala Pro Ala Phe Lys
    290                 295                 300

Gly Trp Leu Ala Asp Gln Asp Val Arg Trp Asn Val Ile Ser Gly Ala
305                 310                 315                 320

Val Asp Asp Arg Thr Pro Lys Glu Arg Gly Val Ala Pro Leu Leu Pro
                325                 330                 335

Lys Tyr Asn Lys Asn Gly Phe Gly Ile Ala Lys Asp Val Gln Asp
            340                 345                 350

Lys Val Leu Glu Ile Pro Lys Ser Arg Tyr Ser Ser Val Asp Leu Phe
        355                 360                 365

Leu Gly Gly Ser Lys Phe Phe Asn Arg Thr Tyr Asn Asp Thr Asn Val
    370                 375                 380

Pro Ile Asn Glu Lys Val Leu Gly Arg Leu Leu Glu Asn Asp Lys Ala
385                 390                 395                 400
```

```
Pro Leu Asp Tyr Asp Leu Ala Lys His Phe Ala His Leu Tyr Ile Arg
            405                 410                 415

Asp Pro Val Ser Thr Phe Glu Glu Leu Leu Asn Gln Asp Asn Lys Thr
        420                 425                 430

Ser Ser Asn His Phe Glu Asn Ile Gln Ser Thr Asn Trp Gln Thr Leu
    435                 440                 445

Arg Phe Lys Pro Pro Thr Gln Gln Ala Thr Pro Asp Lys Lys Asp Ser
450                 455                 460

Pro Gly Trp Arg Val Glu Phe Arg Pro Phe Glu Val Gln Leu Leu Asp
465                 470                 475                 480

Phe Glu Asn Ala Ala Tyr Ser Val Leu Ile Tyr Leu Ile Val Asp Ser
                485                 490                 495

Ile Leu Thr Phe Ser Asp Asn Ile Asn Ala Tyr Ile His Met Ser Lys
            500                 505                 510

Val Trp Glu Asn Met Lys Ile Ala His His Arg Asp Ala Ile Leu Phe
        515                 520                 525

Glu Lys Phe His Trp Lys Ser Phe Arg Asn Asp Thr Asp Val Glu
    530                 535                 540

Thr Glu Asp Tyr Ser Ile Ser Glu Ile Phe His Asn Pro Glu Asn Gly
545                 550                 555                 560

Ile Phe Pro Gln Phe Val Thr Pro Ile Leu Cys Gln Lys Gly Phe Val
                565                 570                 575

Thr Lys Asp Trp Lys Glu Leu Lys His Ser Ser Lys His Glu Arg Leu
            580                 585                 590

Tyr Tyr Tyr Leu Lys Leu Ile Ser Asp Arg Ala Ser Gly Glu Leu Pro
        595                 600                 605

Thr Thr Ala Lys Phe Phe Arg Asn Phe Val Leu Gln His Pro Asp Tyr
610                 615                 620

Lys His Asp Ser Lys Ile Ser Lys Ser Ile Asn Tyr Asp Leu Leu Ser
625                 630                 635                 640

Thr Cys Asp Arg Leu Thr His Leu Asp Asp Ser Lys Gly Glu Leu Thr
                645                 650                 655

Ser Phe Leu Gly Ala Glu Ile Ala Glu Tyr Val Lys Lys Asn Lys Pro
            660                 665                 670

Ser Ile Glu Ser Lys Cys
        675

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gacagtaaaa cgcaggttat                                              20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tctagaagag ttgttatttc                                              20
```

YEAST WITH HIGH CONTENT OF ABU, γ-GLU-ABU, AND/OR γ-GLU-ABU-GLY

TECHNICAL FIELD

The present invention relates to yeast and a yeast extract with a high content of Abu, γ-Glu-Abu, and/or γ-Glu-Abu-Gly. The yeast and yeast extract are useful in the field of foods such as seasonings and health foods.

BACKGROUND ART

Acetolactate synthase is known as an enzyme that catalyzes a reaction of generating acetolactic acid and $CO_2$ from two molecules of pyruvic acid, and a reaction of generating α-acetohydroxybutyric acid and $CO_2$ from pyruvic acid and α-ketobutyric acid (α-KB). As genes encoding acetolactate synthase of yeast, ILV2 and ILV6 are known, and ILV2 and ILV6 encodes the catalytic subunit and regulatory subunit, respectively.

It is known that if acetolactate synthase is deleted from bacteria, the accumulation amount of α-KB in the cells is increased (Non-patent document 1).

It is also known that if expression amount of the ILV2 gene encoding acetolactate synthase, especially the nonSc-ILV2 gene characteristic to beer yeast, is suppressed in brewer's yeasts, the production amounts of the vicinal diketones, especially diacetyl, which diketones serve as off flavors of the products, are decreased (Patent document 1).

α-Aminobutyric acid (Abu) is generated from α-KB by the action of aminotransferase. Therefore, by enhancing the activity of an enzyme that participates in the biosynthesis of Abu, such as α-ketobutyric acid synthetase and aminotransferase, the accumulation amount of Abu or γ-Glu-Abu in the cells can be increased (Patent document 2).

However, any relation between the acetolactate synthase activity and the accumulation amounts of Abu, γ-Glu-Abu, and/or γ-Glu-Abu-Gly in the cells is not known.

PRIOR ART REFERENCES

Patent Documents

Patent document 1: Japanese Patent Laid-open (Kohyo) No. 2009-527218
Patent document 2: WO2012/046731

Non-Patent Document

Non-patent document 1: Bioessays, (3):125-130 (1987)

SUMMARY OF THE INVENTION

Object to be Achieved by the Invention

An object of the present invention is to provide yeast and a yeast extract with a high content of Abu, γ-Glu-Abu, and/or γ-Glu-Abu-Gly.

Means for Achieving the Object

The inventors of the present invention conducted various researches in order to achieve the aforementioned object. As a result, they found that by reducing the activity of acetolactate synthase in yeast of which the activities of α-ketobutyric acid synthetase and aminotransferase were enhanced, the accumulation amounts of Abu, γ-Glu-Abu, and γ-Glu-Abu-Gly in the cells of the yeast was increased, and accomplished the present invention.

The present invention can be thus embodied as follows.

[1]
Yeast having a high content of an α-aminobutyric acid (Abu)-related compound, which yeast has been modified so that intracellular acetolactate synthase activity is decreased, wherein the Abu-related compound consists of one or more kinds of compounds selected from the group consisting of Abu, γ-Glu-Abu, and γ-Glu-Abu-Gly.

[2]
The yeast according to [1], which has been further modified so that the activity or activities of one or more kinds of enzymes selected from the group consisting of α-ketobutyric acid synthetase and aminotransferase is increased.

[3]
The yeast according to [2], wherein the α-ketobutyric acid synthetase is an enzyme encoded by CHA1 gene.

[4]
The yeast according to [2], wherein the aminotransferase is an enzyme encoded by BAT1 gene.

[5]
The yeast according to any one of [1] to [4], which has been further modified so that γ-glutamylcysteine synthetase activity is increased.

[6]
The yeast according to any one of [1] to [5], which is a *Saccharomyces* yeast or *Candida* yeast.

[7]
The yeast according to [6], which is *Saccharomyces cerevisiae* or *Candida utilis*.

[8]
A method for producing a yeast extract, the method comprising preparing a yeast extract by using the yeast according to any one of [1] to [7] as a raw material.

[9]
A method for producing an Abu-related compound, the method comprising:
culturing the yeast according to any one of [1] to [7] in a medium; and
collecting the Abu-related compound from culture.

[10]
The method according to [9], wherein the Abu-related compound is γ-Glu-Abu and/or γ-Glu-Abu-Gly.

BRIEF DESCRIPTION OF THE DRAWINGS

FIG. 1 is a graph showing ILV2 mRNA expression amounts observed when the M007Y strain (parent strain) and the M013Y strain (ILV2 promoter-substituted strain) were each cultured in the SD medium. Data are shown as ratios of the amount of ILV2 mRNA to the amount of ACT1 mRNA as an internal standard.

FIG. 2 is a graph showing Abu, γ-Glu-Abu, and γ-Glu-Abu-Gly contents in the cells observed when the M007Y strain (parent strain) and M013Y strain (ILV2 promoter-substituted strain) were each cultured in the SD medium. Data are shown as contents of the compounds based on dry cell weight (μmol/g-DCW). In the graph, black portions show γ-Glu-Abu content, oblique line portions show Abu content, and gray portions show γ-Glu-Abu-Gly content.

FIG. 3 is a graph showing the ILV2 mRNA expression amounts observed when the M007Y strain, M013Y strain, and M014Y strain (ILV2-disrupted strain) were each cultured in the SD medium containing isoleucine and valine. Data are shown as ratios of the amount of ILV2 mRNA to the amount of ACT1 mRNA as an internal standard.

FIG. 4 is a graph showing Abu, γ-Glu-Abu, and γ-Glu-Abu-Gly contents in the cells observed when the M007Y strain, M013Y strain, and M014Y strain (ILV2-disrupted strain) were each cultured in the SD medium containing isoleucine and valine. Data are shown as contents of the compounds based on dry cell weight (μmol/g-DCW). In the graph, black portions show γ-Glu-Abu content, oblique line portions show Abu content, and gray portions show γ-Glu-Abu-Gly content.

FIG. 5 is a graph showing Abu, γ-Glu-Abu, and γ-Glu-Abu-Gly contents in the cells observed when the M007Y strain, M013Y strain, and M014Y strain (ILV2-disrupted strain) were each cultured in the SDTE medium containing isoleucine and valine. Data are shown as contents of the compounds based on dry cell weight (μmol/g-DCW). In the graph, black portions show γ-Glu-Abu content, oblique line portions show Abu content, and gray portions show γ-Glu-Abu-Gly content.

FIG. 6 is a graph showing Abu, γ-Glu-Abu, and γ-Glu-Abu-Gly contents in the cells observed when the Y006Y strain (parent strain) and M015Y strain (ILV2-disrupted strain) were each cultured in the SD medium containing isoleucine and valine. Data are shown as contents of the compounds based on dry cell weight (μmol/g-DCW). In the graph, black portions show γ-Glu-Abu content, oblique line portions show Abu content, and gray portions show γ-Glu-Abu-Gly content.

FIG. 7 is a graph showing Abu, γ-Glu-Abu, and γ-Glu-Abu-Gly contents in the cells observed when the Y006Y strain (parent strain) and M015Y strain (ILV2-disrupted strain) were each cultured in the SDTE medium containing isoleucine and valine. Data are shown as contents of the compounds based on dry cell weight (μmol/g-DCW). In the graph, black portions show γ-Glu-Abu content, oblique line portions show Abu content, and gray portions show γ-Glu-Abu-Gly content.

MODES FOR CARRYING OUT THE INVENTION

Hereafter, the present invention will be explained in detail.

<1> Yeast of the Present Invention

<1-1> Yeast of the Present Invention

The yeast of the present invention is yeast having a high content of an α-aminobutyric acid (Abu)-related compound, which yeast has been modified so that intracellular acetolactate synthase activity is decreased.

In the present invention, the "Abu-related compound" refers to a compound selected from the group consisting of Abu, γ-Glu-Abu, and γ-Glu-Abu-Gly. In the present invention, Abu and Glu are L-isomers.

The expression "having/with a high content of an Abu-related compound" means that when the yeast of the present invention is cultured in a medium, the yeast produces and accumulates the Abu-related compound in cells thereof in such a degree that the compound can be detected. The yeast of the present invention may be yeast that is able to accumulate an Abu-related compound in the cells in an amount larger than that observed for a non-modified strain. Examples of the non-modified strain include a wild strain and the parent strain of the yeast. The yeast of the present invention may be yeast that is able to accumulate an Abu-related compound in the cells in an amount of 0.4 μmol/g-DCW or more, 1 μmol/g-DCW or more, 2 μmol/g-DCW or more, 3 μmol/g-DCW or more, 5 μmol/g-DCW or more, or 10 μmol/g-DCW or more. In the present invention, one kind of Abu-related compound may be produced and accumulated, or two or more kinds of Abu-related compounds may be produced and accumulated.

The yeast of the present invention can be obtained by modifying an appropriate strain of yeast, for example, any of the strains mentioned later.

The yeast of the present invention may be a budding yeast or fission yeast. Examples of the budding yeast include yeasts belonging to the genus *Saccharomyces* such as *Saccharomyces cerevisiae*, those belonging to the genus *Candida* such as *Candida utilis*, those belonging to the genus *Pichia* such as *Pichia pastoris*, and those belonging to the genus *Hansenula* such as *Hansenula polymorpha*. Examples of the fission yeast include yeasts belonging to the genus *Schizosaccharomyces* such as *Schizosaccharomyces pombe*. Among these, *Saccharomyces cerevisiae* and *Candida utilis* are preferred, which are frequently used for production of yeast extracts. The yeast of the present invention may be haploid yeast, or may be diploid or more polyploid yeast.

Examples of *Saccharomyces cerevisiae* include, for example, the *Saccharomyces cerevisiae* Y006 strain (FERM BP-11299). The Y006 strain was deposited at the National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Aug. 18, 2010 as an international deposit, and assigned an accession number of FERM BP-11299.

Examples of *Saccharomyces cerevisiae* also include, for example, the *Saccharomyces cerevisiae* BY4743 strain (ATCC 201390) and the *Saccharomyces cerevisiae* S288C strain (ATCC 26108). Also, as *Candida utilis*, for example, the *Candida utilis* ATCC 22023 strain can be used. These strains are available from, for example, the American Type Culture Collection (Address: 12301 Parklawn Drive, Rockville, Md. 20852, P.O. Box 1549, Manassas, Va. 20108, United States of America). That is, registration numbers are given to the respective strains, and the strains can be ordered by using these registration numbers (refer to http(colon)//www(dot)atcc(dot)org/). The registration numbers of the strains are listed in the catalogue of the American Type Culture Collection.

<1-2> Reduction of Acetolactate Synthase Activity

The yeast of the present invention has been modified so that intracellular acetolactate synthase activity is decreased.

In the present invention, the "acetolactate synthase" refers to a protein having the activity for catalyzing a reaction of generating α-acetohydroxybutyric acid and $CO_2$ from pyruvic acid and α-ketobutyric acid (α-KB) (EC 2.2.1.6). This activity is also referred to as "acetolactate synthase activity". In the present invention, the acetolactate synthase may have, or may not have the activity for catalyzing a reaction of generating acetolactic acid and $CO_2$ from two molecules of pyruvic acid. The acetolactate synthase activity can be reduced by, for example, disrupting a gene encoding acetolactate synthase. The details of the method for reducing the activity of a protein will be described later.

Examples of the gene encoding acetolactate synthase include the ILV2 gene encoding the catalytic subunit of acetolactate synthase. The protein encoded by the ILV2 gene is also referred to as Ilv2 protein or Ilv2p.

The nucleotide sequence of the ILV2 gene of *Saccharomyces cerevisiae* is disclosed in *Saccharomyces* Genome Database (http(colon)//www(dot)yeastgenome(dot)org/). The ILV2 gene of the *Saccharomyces cerevisiae* S288C strain (ATCC 26108) corresponds to the sequence of 484084 to 486147 in the sequence of the chromosome XIII registered in the NCBI database as GenBank Accession NC_001145. The Ilv2 protein of the *Saccharomyces cerevisiae* S288C strain (ATCC 26108) is registered as GenBank Accession NP_013826. The nucleotide sequence of the ILV2 gene of the *Saccharomyces cerevisiae* S288C strain (ATCC 26108) and the amino acid sequence of the Ilv2 protein encoded by this gene are shown as SEQ ID NOS: 15 and 16, respectively.

Further, for example, the *Saccharomyces cerevisiae* Y006 strain (FERM BP-11299) has two copies of the ILV2 gene.

Reduction of the acetolactate synthase activity can be confirmed by, for example, preparing crude enzyme solutions from the non-modified yeast and the modified yeast, and comparing the acetolactate synthase activities of them. The acetolactate synthase activity can be measured by, for example, a known method (F. C. Stormer and H. E. Umbarger, Biochem. Biophys. Res. Commun., 17, 5, 587-592 (1964)).

The acetolactate synthase may be a variant of the aforementioned acetolactate synthase such as a protein containing the amino acid sequence of SEQ ID NO: 16, so long as the original function is maintained. Such a variant may be called "conservative variant". Examples of the conservative variant include, for example, homologues and artificially modified versions of the aforementioned acetolactate synthase such as a protein containing the amino acid sequence of SEQ ID NO: 16.

The expression that "the original function is maintained" means that a variant of a protein has an activity corresponding to the activity of the original protein. That is, the expression that "the original function is maintained" used for acetolactate synthase means that the variant of the protein has the acetolactate synthase activity.

A gene encoding a homologue of the aforementioned acetolactate synthase can be easily obtained from public databases by, for example, BLAST search or FASTA search using any of the aforementioned nucleotide sequences of the genes encoding acetolactate synthase as a query sequence. Further, a gene encoding a homologue of the aforementioned acetolactate synthase can also be obtained by, for example, PCR using a chromosome of yeast as the template, and oligonucleotides prepared on the basis of any one of the known gene sequences as primers.

The gene encoding a conservative variant of acetolactate synthase may be, for example, such a gene as mentioned below. That is, the gene encoding acetolactate synthase may also be a gene encoding a protein having the aforementioned amino acid sequence including substitution, deletion, insertion or addition of one or several amino acid residues at one or several positions, so long as it encodes a protein having the acetolactate synthase activity. In such a case, usually 70% or more, preferably 80% or more, more preferably 90% or more, of the corresponding activity is maintained in the variant protein, relative to the protein before including addition, deletion, insertion, or addition of one or several amino acid residues. Although the number of "one or several" may differ depending on the positions in the three-dimensional structure of the protein or types of amino acid residues, specifically, it is 1 to 50, 1 to 40, or 1 to 30, preferably 1 to 20, more preferably 1 to 10, still more preferably 1 to 5.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation due to an individual difference, or a difference of species of the organism from which the gene is derived (mutant or variant).

Furthermore, the gene having such a conservative mutation as mentioned above may be a gene coding for a protein showing a homology of 80% or more, preferably 90% or more, more preferably 95% or more, still more preferably 97% or more, particularly preferably 99% or more, to the total amino acid sequence mentioned above, and having the acetolactate synthase activity. In this description, "homology" may mean "identity".

Further, the gene encoding acetolactate synthase may be a DNA that is able to hybridize under stringent conditions with a probe that can be prepared from a known gene sequence, such as a sequence complementary to a part or the whole of the aforementioned nucleotide sequence, and which DNA codes for a protein having the acetolactate synthase activity. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C.

As described above, the probe used for the aforementioned hybridization may be a part of a sequence that is complementary to a gene. Such a probe can be prepared by PCR using oligonucleotides prepared on the basis of a known gene sequence as the primers and a DNA fragment containing any of the these nucleotide sequences as the template. For example, when a DNA fragment having a length of about 300 bp is used as the probe, the washing conditions of the hybridization may be, for example, 50° C., 2×SSC and 0.1% SDS.

Further, the gene encoding acetolactate synthase may be a gene in which an arbitrary codon is replaced with an equivalent codon.

The above descriptions concerning conservative variants of genes and proteins can also be applied mutatis mutandis to arbitrary proteins such as Cha1 protein, and genes encoding them.

<1-3> Other Modifications

The yeast of the present invention may further have another modification. The other modification can be appropriately chosen according to the type of the Abu-related compound to be generated and accumulated, and so forth. In the present invention, modifications for constructing the yeast of the present invention can be performed in an arbitrary order.

For example, the yeast of the present invention may have been modified so that the Abu biosynthesis ability thereof is enhanced. It is expected that the contained amount of the Abu-related compound in the cells is increased by such a modification. The Abu biosynthesis ability can be enhanced by increasing the activity of an enzyme that participates in the biosynthesis of Abu. Examples of the enzyme that participates in the biosynthesis of Abu include α-ketobutyric acid synthetase and aminotransferase. In the present invention, the activity of one kind of enzyme that participates in the biosynthesis of Abu may be enhanced, or the activities of two or more kinds of enzymes that participate in the biosynthesis of Abu may be enhanced. The activity of an enzyme can be increased by, for example, enhancing the expression of the gene encoding the enzyme. Details of the method for increasing the activity of a protein will be described later.

The "α-ketobutyric acid synthetase" mentioned herein refers to a protein having the activity for catalyzing a reaction of generating α-ketobutyric acid from L-threonine. Examples of the α-ketobutyric acid synthetase include, for example, serine/threonine deaminase and threonine deaminase. Examples of the gene encoding serine/threonine deaminase include the CHA1 gene. Examples of the gene encoding threonine deaminase include the ILV1 gene. It is preferred that, for example, the activity of serine/threonine deaminase encoded by the CHA1 gene, among these, is enhanced. In the present invention, the activity of one kind of α-ketobutyric acid synthetase may be increased, or activities of two or more kinds of α-ketobutyric acid synthetases may be increased.

The nucleotide sequences of the CHA1 gene (systematic name: YCL064C) and the ILV1 gene (systematic name: YER086W) of Saccharomyces cerevisiae are disclosed in Saccharomyces Genome Database (http(colon)//www(dot)yeastgenome(dot)org/). The nucleotide sequence of the CHA1 gene of the Saccharomyces cerevisiae S288C strain (ATCC 26108) and the amino acid sequence of the Cha1 protein encoded by this gene are shown as SEQ ID NOS: 17 and 18, respectively. The nucleotide sequence of the ILV1 gene of the Saccharomyces cerevisiae S288C strain (ATCC 26108) and the amino acid sequence of the Ilv1 protein encoded by this gene are shown as SEQ ID NOS: 19 and 20, respectively.

The "aminotransferase" mentioned herein refers to a protein having an activity for catalyzing a reaction of generating Abu from α-ketobutyric acid by transamination. Examples of aminotransferase include, for example, alanine:glyoxylate aminotransferase, branched-chain amino acid transaminase, aspartate aminotransferase, and γ-aminobutyrate transaminase. Examples of the gene encoding alanine:glyoxylate aminotransferase include the AGX1 gene. Examples of the gene encoding branched-chain amino acid transaminase include the BAT1 and BAT2 genes. Examples of the gene encoding aspartate aminotransferase include the AAT1 and AAT2 genes. Examples of the gene encoding γ-aminobutyrate transaminase include the UGA1 gene. It is preferable to increase, for example, the activity of the branched-chain amino acid transaminase encoded by BAT1, among these. In the present invention, the activity of one kind of aminotransferase may be increased, or the activities of two or more kinds of aminotransferases may be increased.

The nucleotide sequences of the AGX1 (systematic name: YFL030W), BAT1 (systematic name: YHR208W), BAT2 (systematic name: YJR148W), AAT1 (systematic name: YKL106W), AAT2 (systematic name: YLR027C), and UGA1 (systematic name: YGR019W) genes of Saccharomyces cerevisiae are disclosed in Saccharomyces Genome Database (http(colon)//www(dot)yeastgenome(dot)org/). The nucleotide sequence of the BAT1 gene of the Saccharomyces cerevisiae S288C strain (ATCC 26108) and the amino acid sequence of the Bat1 protein encoded by this gene are shown as SEQ ID NOS: 21 and 22, respectively.

Further, the yeast of the present invention may also have been modified so that intracellular activity of γ-glutamylcysteine synthetase is increased or reduced. The "γ-glutamylcysteine synthetase" mentioned herein may refer to a protein having an activity for recognizing L-Glu and Abu as substrates and catalyzing a reaction of generating γ-Glu-Abu. The γ-glutamylcysteine synthetase may have, or may not have an activity for recognizing L-Glu and L-Cys as substrates, and catalyzing a reaction of generating γ-glutamylcysteine (γ-Glu-Cys). For example, when γ-Glu-Abu and/or γ-Glu-Abu-Gly are generated and accumulated in the cells, the activity of γ-glutamylcysteine synthetase may be increased. Further, for example, when γ-Glu-Abu and/or γ-Glu-Abu-Gly are not generated and accumulated in the cells, the activity of γ-glutamylcysteine synthetase may be reduced. Enhancement of the activity of γ-glutamylcysteine synthetase is disclosed in, for example, U.S. Pat. No. 7,553,638; Yasuyuki Otake et al., Bioscience and Industry, Vol. 50, No. 10, pages 989-994, 1992, etc.

The yeast of the present invention may also have been modified so that intracellular activity of glutathione synthase is increased or reduced. The "glutathione synthase" mentioned herein may refer to a protein having an activity for recognizing γ-Glu-Abu and Gly as substrates, and catalyzing a reaction of generating γ-Glu-Abu-Gly. The glutathione synthase may have, or may not have an activity for recognizing γ-Glu-Cys and Gly as substrates, and catalyzing a reaction of generating glutathione (γ-Glu-Cys-Gly). For example, when γ-Glu-Abu-Gly is generated and accumulated in the cells, the activity of glutathione synthase may be increased. Further, for example, when γ-Glu-Abu-Gly is not generated and accumulated in the cells, the activity of glutathione synthase may be reduced.

Examples of the gene encoding γ-glutamylcysteine synthetase include the GSH1 gene. Examples of the gene encoding glutathione synthase include the GSH2 gene. The nucleotide sequences of the GSH1 gene and GSH2 gene of Saccharomyces cerevisiae are disclosed in Saccharomyces Genome Database (http(colon)//www(dot)yeastgenome(dot)org/). Further, the nucleotide sequences of GSH1 gene and GSH2 gene of Candida utilis are disclosed in U.S. Pat. No. 7,553,638. The nucleotide sequence of the GSH1 gene of the Saccharomyces cerevisiae S288C strain (ATCC 26108) and the amino acid sequence of the Gsh1 protein encoded by this gene are shown as SEQ ID NOS: 23 and 24, respectively.

Further, the yeast of the present invention may also have been modified so that intracellular activity of peptidase is reduced. The "peptidase" referred to herein may refer to a protein having an activity for catalyzing a reaction of hydrolyzing γ-Glu-Abu and/or γ-Glu-Abu-Gly. Examples of the peptidase include, for example, the proteins encoded by DUG1 gene, DUG2 gene, DUG3 gene, and ECM38 gene (Japanese Patent Laid-open (Kokai) No. 2012-213376). Dug1p, Dug2p, and Dug3p encoded by the DUG1 gene, DUG2 gene, and DUG3 gene, respectively, form a DUG complex and function. It is known that all of Dug1p, Dug2p, and Dug3p are required for the decomposition of glutathione by the DUG complex (Ganguli D. et al., Genetics, 2007 March; 175(3):1137-51), and the activity of the DUG complex can be reduced by reducing the activity or activities of one or more kinds of proteins selected from Dug1p, Dug2p, and Dug3p. It is preferable to reduce at least the activity of Dug2p among them. In the present invention, the activity of one kind of peptidase may be reduced, or the activities of two or more kinds of peptidases may be reduced. The nucleotide sequences of the DUG1 gene, DUG2 gene, DUG3 gene, and ECM38 gene of *Saccharomyces cerevisiae* are disclosed in *Saccharomyces* Genome Database (http(colon)//www(dot)yeastgenome(dot)org/).

The genes used for these "other modifications" are also not limited to the genes exemplified above or genes having a known nucleotide sequence, but may be variants thereof, so long as proteins that maintain the original function are encoded. To such variants of genes or proteins, the aforementioned descriptions concerning conservative variants of the acetolactate synthase and the gene encoding it can be applied, mutatis mutandis. When a protein functions as a complex consisting of a plurality of subunits, the expression "the original function is maintained" used for each subunit may mean that each subunit can form the complex together with the other subunits, and the complex has the corresponding activity. That is, for example, the expression "the original function is maintained" used for each subunit of the DUG complex may mean that each subunit can form the complex together with the other subunits, and the complex has the peptide decomposition activity.

Such various modifications as mentioned above can be performed by mutagenesis treatments or genetic engineering techniques. Genetic engineering techniques for *Saccharomyces cerevisiae* are specifically described in many books. Moreover, various kinds of methods have been reported also for *Candida utilis* in recent years, and they can be used. For example, specific methods are described in such prior references as Norihiko Misawa, Chemical Engineering, June, 1999, pp. 23-28; Luis Rodriguez et al., FEMS Microbiology Letters, 165, 335-340 (1998); WO98/07873; Japanese Patent Laid-open (Kokai) No. 8-173170; WO95/32289; Keiji Kondo et al., Journal of Bacteriology, Vol. 177, No. 24, pp. 7171-7177 (1995); WO98/14600; Japanese Patent Laid-open (Kokai) Nos. 2006-75122, 2006-75123, 2007-089441, and 2006-101867, and these can be referred to as required.

<1-4> Methods for Increasing Activity of Protein

Hereafter, the methods for increasing the activity of a protein will be explained.

The expression "the activity of a protein is increased" means that the activity of the protein per cell is increased as compared with that of a non-modified strain such as a wild-type strain and parent strain. The state that "the activity of a protein is increased" may also be expressed as "the activity of a protein is enhanced". Specifically, the expression "the activity of a protein is increased" means that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) coding for the protein, or the translation amount of the protein (i.e. the amount of the protein). Further, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Further, so long as the activity of the protein is eventually increased, the activity of an objective protein inherently contained in yeast may be attenuated and/or eliminated, and then an appropriate type of the objective protein may be imparted to the host.

Although the degree of the increase in the activity of a protein is not particularly limited so long as the activity of the protein is increased as compared with a non-modified strain, the activity of the protein may be increased 1.5 times or more, 2 times or more, or 3 times or more, as compared with that of a non-modified strain. Further, when the non-modified strain does not have the activity of the objective protein, it is sufficient that the protein is produced as a result of introduction of the gene encoding the protein, and for example, the protein may be produced to such an extent that the enzyme activity can be measured.

The modification for increasing the activity of a protein is attained by, for example, increasing the expression of a gene coding for the protein. The state that "the expression of a gene is increased" may also be referred to as "the expression of a gene is enhanced". The expression of a gene may be increased 1.5 times or more, 2 times or more, or 3 times or more, as compared with that of a non-modified strain. Further, the state that "the expression of a gene is increased" includes not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (MillerI, J. H., Experiments in Molecular Genetics, 1972, Cold Spring Harbor Laboratory). Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include autonomously replicating sequence (ARS), which consists of characteristic short repetitive sequences, and rDNA sequences, which exist in a copy number of about 150. An example of transformation of yeast using a plasmid containing ARS is disclosed in WO95/32289. Further, a gene can be incorporated into a transposon, and the transposon can be transferred into a chromosome so that many copies of the gene are introduced.

Introduction of a target gene into a chromosome can be confirmed by Southern hybridization using a probe having a sequence complementary to the whole gene or a part thereof, PCR using primers prepared on the basis of the sequence of the gene, or the like.

Further, the copy number of a target gene can also be increased by introducing a vector containing the gene into a host microorganism. For example, the copy number of a target gene can be increased by ligating a DNA fragment containing the target gene with a vector that functions in a host microorganism to construct an expression vector of the gene, and transforming the host microorganism with the expression vector. The DNA fragment containing the target gene can be obtained by, for example, PCR using a genomic DNA of a microorganism having the target gene as the template. As the vector, a vector autonomously replicable in the cell of the host microorganism can be used. The vector is preferably a multi-copy vector. Examples of the vector that functions in a yeast cell include, for example, a plasmid having the replication origin of CEN4, and a multi-copy plasmid having the replication origin of 2 μm DNA. Specific examples of the vector that functions in a yeast cell include, for example, pAUR123 (Takara Bio) and pYES2 (Invitrogen).

When a gene is introduced, it is sufficient that the gene is expressibly harbored by the yeast of the present invention. Specifically, it is sufficient that the gene is introduced so that it is expressed under control by a promoter sequence that functions in the yeast of the present invention. The promoter may be a promoter derived from the host, or a heterogenous promoter. The promoter may be the native promoter of the gene to be introduced, or a promoter of another gene. The promoter may be a promoter originally carried by the vector to be used. As the promoter, for example, such a stronger promoter as mentioned later may also be used.

Further, when two or more of genes are introduced, it is sufficient that the genes each are expressibly harbored by the yeast of the present invention. For example, all the genes may be carried by a single expression vector or a chromosome. Further, the genes may be separately carried by two or more expression vectors, or separately carried by a single or two or more expression vectors and a chromosome. An operon constituted by two or more genes may also be introduced. The case of "introducing two or more genes" include, for example, cases of introducing respective genes encoding two or more kinds of enzymes, introducing respective genes encoding two or more subunits constituting a single enzyme, and a combination of the foregoing cases.

The gene to be introduced is not particularly limited so long as it codes for a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene.

In addition, when a protein functions as a complex consisting of a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that code for the subunits may be enhanced. It is usually preferable to enhance the expression of all of the plurality of genes coding for the subunits. Further, the subunits constituting the complex may be derived from a single kind of organism or two or more kinds of organisms, so long as the complex has a function of the objective protein. That is, for example, genes of the same organism coding for a plurality of subunits may be introduced into a host, or genes of different organisms coding for a plurality of subunits may be introduced into a host.

The expression of a gene can also be increased by improving the transcription efficiency of the gene. The transcription efficiency of a gene can be improved by, for example, replacing the promoter of the gene on a chromosome with a stronger promoter. The "stronger promoter" refers to a promoter that provides an improved transcription of a gene as compared with an inherently existing wild-type promoter of the gene. Examples of stronger promoters include, for example, the known high expression promoters, i.e., promoters of the PGK1, PDC1, TDH3, TEF1, HXT7, ADH1 genes, and so forth. Further, as the stronger promoter, a highly-active type of an existing promoter may also be obtained by using various reporter genes.

The expression of a gene can also be increased by improving the transcription efficiency of the gene. The translation efficiency of a gene can be improved by, for example, modifying codons. That is, in the case of heterogenous expression of a gene or the like, the translation efficiency of the gene can be improved by replacing a rare codon present in the gene with a synonymous codon more frequently used. Codons can be replaced by, for example, the site-specific mutation method for introducing an objective mutation into an objective site of DNA. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)). Alternatively, a gene fragment in which objective codons are replaced may be totally synthesized. Frequencies of codons in various organisms are disclosed in the "Codon Usage Database" (http(colon)//www(dot)kazusa (dot)or(dot)jp/codon; Nakamura, Y. et al, Nucl. Acids Res., 28, 292 (2000)).

Further, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Further, the modification that increases the activity of a protein can also be attained by, for example, enhancing the specific activity of the enzyme. Enhancement of the specific activity also includes attenuation or elimination of feedback inhibition. A protein showing an enhanced specific activity can be obtained by, for example, searching various organisms. Further, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Further, a random mutation may be induced by directly treating DNA in vitro with hydroxylamine. Enhancement of the specific activity may be independently used, or may be used in an arbitrary combination with such methods for enhancing gene expression as mentioned above.

When the yeast of the present invention has a polyploidy of diploidy or higher ploidy, and the activity of a protein is increased by modification of a chromosome, the yeast of the present invention may be a heteroploid having a chromosome modified so that the activity of the protein is increased, and a wild-type chromosome, or may be a homoploid having chromosomes modified so that the activity of the protein is increased, so long as the activity of the protein is eventually increased.

As the method of transforming yeast, there can be used methods usually used for transformation of yeast, such as the protoplast method, KU method (H. Ito et al., J. Bateriol., 153-163 (1983)), KUR method (Fermentation and Industry, vol. 43, pp. 630-637 (1985)), electroporation method (Luis et al., FEMS Microbiology Letters, 165 (1998) 335-340), and method using a carrier DNA (Gietz R. D. and Schiestl R. H., Methods Mol. Cell. Biol., 5:255-269 (1995)). Further, methods for manipulating yeast such as methods for sporeforming and methods for isolating monoploid yeast are described in "Chemical and Biological Experimental Line, 31, Experimental Technique for Yeast", first edition, Hirokawa Publishing; "Biomanual Series 10, Method of Genetic Experiment using Yeast", first edition, Yodosha; and so forth.

An increase in the activity of a protein can be confirmed by measuring the activity of the protein.

An increase in the activity of a protein can also be confirmed by confirming an increase in the expression of a gene coding for the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

The aforementioned methods for increasing the activity of a protein can be used for enhancement of the activities of arbitrary proteins such as aminotransferase, and enhancement of the expression of arbitrary genes such as genes encoding those arbitrary proteins.

<1-5> Method for Reducing Activity of Protein

Hereafter, the methods for reducing the activity of a protein will be explained.

The expression "the activity of a protein is reduced" means that the activity of the protein per cell is reduced as compared with that of a non-modified strain such as a wild-type strain and parent strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) coding for the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. Although the degree of the reduction in the activity of a protein is not particularly limited, so long as the activity is reduced as compared with that of a non-modified strain, the activity of a protein may be reduced to, for example, 50% or less, 20% or less, 10% or less, 5% or less, or 0% of that of a non-modified strain.

The modification for reducing the activity of a protein is attained by, for example, reducing the expression of a gene coding for the protein. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as promoter. When an expression control sequence is modified, preferably one or more nucleotides, more preferably two or more nucleotides, particularly preferably three or more nucleotides, of the expression control sequence are modified. Further, the promoter of a gene on a chromosome may be replaced with a weaker promoter. The "weaker promoter" means a promoter providing an attenuated transcription of the gene compared with an inherently existing wild-type promoter of the gene. As such a weaker promoter, for example, various inducible promoters can be used. That is, inducible promoters can function as a weaker promoter in the absence of the inducer. Examples of the inducible promoters include, for example, the galactose-inducible promoter of the galactokinase gene (GAL1). Further, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth.

The modification for reducing the activity of a protein can also be attained by, for example, disrupting a gene coding for the protein. Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Further, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, preparing a deficient type gene modified via deletion of a partial sequence thereof so that it is unable to produce a protein that normally functions, and transforming a microorganism with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easier. The protein encoded by the deficient type gene has a conformation different from that of the wild-type protein, even if it is produced, and thus the function thereof is reduced or eliminated.

Depending on the structure of the recombinant DNA to be used, insertion may occur so that the wild-type gene and the deletion type gene is contained in a chromosome together with another part of the recombinant DNA (for example, vector moiety and marker gene) flanked by them, as a result of the homologous recombination. Since the wild type gene functions in that state, it is necessary to induce homologous recombination again between two of the genes to eliminate one copy of the gene from the chromosomal DNA together with the vector moiety and the marker gene, and select a strain in which the deletion type gene remains.

Further, for example, by transforming yeast with a linear DNA containing an arbitrary sequence as well as upstream and downstream sequences of a substitution target site on a chromosome at the respective ends of the arbitrary sequence so as to cause homologous recombination at each of the upstream and downstream of the substitution target site, the substitution target site can be replaced with the arbitrary sequence in one step. As the arbitrary sequence, for example, a sequence containing a marker gene can be used. The marker gene may be removed thereafter as required. When the marker gene is removed, the sequences for the homologous recombination may be added to the both ends of the marker gene so that the marker gene can be efficiently removed.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex consisting of a plurality of subunits, a part or all of the plurality of subunits may be modified, so long as the activity of the protein is eventually reduced. That is, for example, a part or all of a plurality of genes that code for the respective subunits may be disrupted or the like. Further, when there is a plurality of isozymes of a protein, a part or all of the activities of the plurality of isozymes may be reduced, so long as the activity of the protein is eventually reduced. That is, for example, a part or all of a plurality of genes that code for the respective isozymes may be disrupted or the like. Further, for example, a part of the plurality of the genes encoding the isozymes may be disrupted, and the expression of the remaining gene(s) may be reduced.

When the yeast of the present invention has a polyploidy of diploidy or higher ploidy, the yeast of the present invention may be a heteroploid having a chromosome modified so that the activity of a protein is reduced, and a wild-type chromosome, or a homoploid having chromosomes modified so that the activity of a protein is reduced, so long as the activity of the protein is eventually reduced. It is usually preferred that the yeast of the present invention is a homoploid having chromosomes modified so that the activity of a protein is reduced.

A reduction in the activity of a protein can be confirmed by measuring the activity of the protein.

A reduction in the activity of a protein can also be confirmed by confirming a reduction in the expression of a gene coding for the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA is preferably reduced to, for example, 50% or less, 20% or less, 10% or less, 5% or less, or 0%, of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably reduced to, for example, 50% or less, 20% or less, 10% or less, 5% or less, or 0%, of that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein as mentioned above can be applied to reduction in the activities of arbitrary proteins such as acetolactate synthase, and reduction in the expression of arbitrary genes such as genes encoding those arbitrary proteins.

<2> Method for Producing Yeast Extract

The yeast of the present invention can be used as a raw material for producing yeast extract. That is, the present invention provides a method for producing a yeast extract, the method comprising preparing a yeast extract by using the yeast of the present invention as a raw material. The yeast extract produced by using the yeast of the present invention as a raw material is also called "yeast extract of the present invention". The yeast extract of the present invention can be produced in the same manner as that used for the production of usual yeast extracts except that the yeast of the present invention is used as a raw material. Hereafter, the method for producing the yeast extract of the present invention will be explained.

First, the yeast of the present invention is cultured in a medium. The medium to be used is not particularly limited, so long as the yeast of the present invention can proliferate therein, and an Abu-related compound is generated and accumulated therein. As the medium, for example, a usual medium used for culture of yeast can be used. Specific examples of the medium include, for example, but are not limited to, the SD medium, SG medium, and SDTE medium. As the medium, for example, a medium containing component(s) selected from carbon source, nitrogen source, phosphate source, sulfur source, and other various organic components and inorganic components as required can be used. The types and concentrations of the medium components may be appropriately determined according to various conditions such as the type of yeast to be used and the type of the Abu-related compound to be generated and accumulated.

The carbon source is not particularly limited, so long as the yeast of the present invention can utilize it to generate an Abu-related compound. Specific examples of the carbon source include, for example, saccharides such as glucose, fructose, sucrose, lactose, galactose, xylose, arabinose, blackstrap molasses, hydrolysate of starches, and hydrolysates of biomass, organic acids such as acetic acid, fumaric acid, citric acid, succinic acid, and malic acid, alcohols such as glycerol, crude glycerol, and ethanol, and fatty acids. As the carbon source, one kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition product, ammonia, and urea. As the nitrogen source, one kind of nitrogen source may be used, or two or more kinds of nitrogen sources may be used in combination.

Specific examples of the phosphate source include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of other various organic and inorganic components include, for example, inorganic salts such as sodium chloride and potassium chloride; trace metals such as iron, manganese, magnesium and calcium; vitamins such as vitamin B1, vitamin B2, vitamin B6, nicotinic acid, nicotinamide, and vitamin 312; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Further, when an auxotrophic mutant strain that requires an amino acid or the like for growth thereof is used, it is preferable to supplement a required nutrient to the medium. For example, for culturing a strain of which acetolactate synthase activity is reduced, a medium supplemented with isoleucine and valine is preferably used.

Although the yeast of the present invention can generate and accumulate an Abu-related compound in the cells thereof even when it is cultured in a medium not supplemented with any Abu-related compound, an Abu-related compound may be supplemented to the medium. One kind of Abu-related compound or two or more kinds of Abu-related compounds may be supplemented to the medium.

Culture conditions are not particularly limited, so long as the yeast of the present invention can proliferate, and an Abu-related compound is generated and accumulated. The culture can be performed with, for example, usual conditions used for culture of yeast. The culture conditions may be appropriately determined according to various conditions such as the type of yeast to be used and the type of the Abu-related compound to be generated and accumulated.

The culture can be performed, for example, aerobically as aeration culture or shaking culture by using a liquid medium. The culture temperature may be, for example, 25 to 35° C., preferably 27 to 33° C., more preferably 28 to 32° C. The culture period may be, for example, 5 hours or longer, 10 hours or longer, or 15 hours or longer, and may be 120 hours or shorter, 72 hours or shorter, or 48 hours or shorter. The culture can be performed as batch culture, fed-batch culture, continuous culture, or a combination of these.

By culturing the yeast of the present invention as described above, an Abu-related compound is accumulated in the cells of the yeast, and yeast with a high content of an Abu-related compound is obtained.

A yeast extract can be prepared from the obtained yeast in the same manner as that used for the preparation of usual yeast extract. The yeast extract may be one obtained by hot water extraction of the yeast cells and following treatments, or one obtained by digestion of the yeast cells and following treatments. The obtained yeast extract may be concentrated, or dried into powder, as required.

A yeast extract with a high content of an Abu-related compound (yeast extract of the present invention) is obtained as described above. The yeast extract of the present invention contains a certain amount of an Abu-related compound in terms of dry weight based on the total solid content in the yeast extract. The yeast extract of the present invention may contain, for example, Abu, in an amount of preferably 0.1% by weight or more, more preferably 0.5% by weight or more, still more preferably 1.0% by weight or more, particularly preferably 5.0% by weight or more. The yeast extract of the present invention may contain, for example, γ-Glu-Abu, in an amount of preferably 0.1% by weight or more, more preferably 1.0% by weight or more, still more preferably 2.0% by weight or more, particularly preferably 20% by weight or more. The yeast extract of the present invention may contain, for example, γ-Glu-Abu-Gly, in an amount of preferably 0.1% by weight or more, more preferably 0.5% by weight or more, still more preferably 1.0% by weight or more, particularly preferably 2% by weight or more.

<3> Method for Producing Abu-Related Compound

The Abu-related compound may also be collected from culture of the yeast of the present invention. That is, the present invention provides a method for producing an Abu-related compound, the method comprising culturing the yeast of the present invention in a medium, and collecting the Abu-related compound from culture. The culture method is as described above. In the present invention, for example, an Abu-related compound accumulated in the cells can be collected. When an Abu-related compound is accumulated also in the medium, the Abu-related compound accumulated in the medium may also be collected.

The Abu-related compound can be collected by known methods used for separation and purification of compounds. Examples of such methods include, for example, ion-exchange resin method, membrane treatment, precipitation, and crystallization. These methods can be used in combination as required. When the Abu-related compound accumulated in the cells is collected, for example, the cells can be disrupted with ultrasonic waves or the like, the cells can be removed from the cell-disrupted suspension by centrifugation, and then the Abu-related compound can be collected by the ion exchange resin method or the like from the thus-obtained supernatant. The collected Abu-related compound may be a free compound, a salt thereof, or a mixture of them.

The salt is not particularly limited so long as it is orally ingestible. Specific examples of the salt at an acidic group such as carboxyl group include ammonium salt, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine, and dicyclohexylamine, and salts with basic amino acids such as arginine and lysine. Specific examples of the salt at a basic group such as amino group include salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, malic acid, and methylmalonic acid, and salts with organic sulfonic acid such as methanesulfonic acid, benzenesulfonic acid, and p-toluenesulfonic acid. As the salt, one kind of salt may be used, or two or more kinds of salts may be used in combination.

The collected Abu-related compound may also contain component(s) such as, for example, yeast cells, medium components, moisture, and by-product metabolites of yeast, in addition to the Abu-related compound. Purity of the collected Abu-related compound may be, for example, 30% (w/w) or higher, 50% (w/w) or higher, 70% (w/w) or higher, 80% (w/w) or higher, 90% (w/w) or higher, or 95% (w/w) or higher.

<4> Food or Drink of the Present Invention

The Abu-related compound and/or yeast extract obtained as described above can be used for manufacture of foods and drinks. That is, the present invention provides a method for producing a food or drink, the method comprising adding an Abu-related compound and/or yeast extract obtained by the aforementioned method to a food or drink or a raw material thereof. A food or drink produced as described above is also referred to as "food or drink of the present invention". Further, in an embodiment, "kokumi" can be imparted to a food or drink by adding the Abu-related compound and/or the yeast extract. Examples of the food or drink include, for example, alcoholic beverages, breads, and fermented food seasonings.

The food or drink of the present invention can be produced in the same manner by using the same raw materials as those used for usual foods or drinks except that the Abu-related compound and/or the yeast extract is added. Examples of such raw materials include, for example, rice, barley, cornstarch, etc. for alcoholic beverages, wheat flour, sugar, salt, butter, fermentation yeast, etc. for breads, and soybean, wheat, etc. for fermented food seasonings. The Abu-related compound and/or the yeast extract may be added at any stage of the manufacturing process of food or drink. That is, the Abu-related compound and/or the yeast extract may be added to a raw material of a food or drink, a food or drink under the manufacture, or a completed food or drink. Further, the yeast extract, a concentrated product thereof, or dried product thereof per se can also be used as a fermented food seasoning.

The addition amount of the Abu-related compound and/or the yeast extract is not particularly limited, and can be appropriately determined according to various conditions such as the type of the food or drink and the mode of ingestion of the food or drink. The Abu-related compound and/or the yeast extract may be added to a food or drink or a raw material thereof in an amount of, for example, 1 ppm (w/w) or more, 100 ppm (w/w) or more, or 1% (w/w) or more, in terms of the amount of the Abu-related compound. Further, the Abu-related compound and/or the yeast extract may be added to a food or drink, or a raw material thereof in an amount of, for example, 100% (w/w) or less, 10% (w/w) or less, or 1% (w/w) or less, in terms of the amount of the Abu-related compound.

EXAMPLES

Hereafter, the present invention will be still more specifically explained with reference to examples.

<Example 1> Construction of M013Y Strain with Enhanced Activity of 2-Aminobutyric Acid Biosynthesis System Enzyme, and Attenuated Expression of Acetolactate Synthase Gene (ILV2)

There was constructed a yeast strain (M013Y strain) in which the activity of 2-aminobutyric acid biosynthesis system enzyme was enhanced, and the expression of the gene encoding acetolactate synthase (ILV2) was attenuated by the following method for the purpose of enhancing 2-aminobutyric acid-producing ability.

The *Saccharomyces cerevisiae* AG1 ura3-strain (Japanese Patent Laid-open (Kokai) No. 2012-213376) was used as the parent strain. The AG1 ura3-strain is a γ-glutamylcysteine synthetase gene (GSH1) expression-enhanced strain of the *Saccharomyces cerevisiae* Y006 strain (FERM BP-11299). The AG1 ura3-strain is deficient in the URA3 gene, and shows uracil auxotrophy.

According to the method of Sofyanovich et al. (Olga A. Sofyanovich et al., A New Method for Repeated "Self-Cloning" Promoter Replacement in *Saccharomyces cerevisiae*, Mol. Biotechnol., 48, 218-227 (2011)), there was prepared a strain corresponding to the AG1 ura3-strain in which the promoter of the branched chain amino acid aminotransferase gene (BAT1) was replaced with the promoter region of glyceraldehyde triphosphate dehydrogenase gene (TDH3) (henceforth referred to as pTDH3), which is a constitutive expression promoter. The method was as follows. PCR was performed by using the primer of SEQ ID NO: 1

(5'-GCCAGGCGGTTGATACTTTGTGCAGATTTCATACCGGCTGTCGCT

ATTATTACTGATGAATTGGCTCTCTTTTTGTTTAATCTTAACCCAACTG

CACAGA-3')

having an upstream sequence of BAT1 at the 5' end, the primer of SEQ ID NO: 2

(5'-TTGGATGCATCTAATGGGGCACCAGTAGCGAGTGTTCTGATGGAG

AATTTCCCCAACTTCAAGGAATGTCTCTGCAACATTTGTTTATGTGTGT

TTATTC-3')

having an internal partial sequence of ORF of the BAT1 gene starting from the start codon, and the pUC19-URA3-pTDH3-URA3 plasmid (described in the aforementioned report of Sofyanovich) as the template to obtain a DNA fragment having URA3 flanked with TDH3 promoters. The conditions for PCR were 94° C. for 10 sec (thermal denaturation), 60° C. for 10 sec (annealing), and 72° C. for 4 min (extension) for 25 cycles. The AG1 ura3-strain was transformed with this DNA fragment, and applied to an SD plate medium not containing uracil. From grown transformants, a strain in which the BAT1 promoter was replaced by pTDH3-URA3-pTDH3 was obtained. The preparation method of the SD medium is shown below. The SD plate medium was prepared by adding 2% of Bacto agar to the SD medium.

[Composition of SD medium]

| D(+)-glucose | 20 g |
| 10 × YNB | 100 mL |
| MilliQ water | up to 1 L |
| | 1 L |

The SD medium was prepared by mixing glucose sterilized by autoclaving and YNB sterilized by filter sterilization in the aforementioned composition, and diluting the mixture with MilliQ water sterilized by autoclaving to the total volume.

10×YNB was prepared as follows. Difco Yeast Nitrogen Base w/o Amino Acids and Ammonium Sulfate (17 g) and ammonium sulfate (50 g) were dissolved in MilliQ water (1 L), and the solution was adjusted to pH 5.2, and sterilized by filter sterilization. The resultant was kept in a cool dark place in order to prevent decomposition of vitamins.

Since a URA3 gene-deficient strain shows 5-fluoroorotic acid (5-FOA) resistance, a strain from which URA3 selection marker is eliminated can be selected by using a medium containing 5-FOA. Therefore, a strain in which the BAT1 promoter was replaced by pTDH3-URA3-pTDH3 was cultured overnight in the SD medium containing uracil, and applied in an appropriate amount to 5-FOA plate medium. From the grown colonies, a strain in which URA3 was eliminated by the homologous recombination of the introduced two TDH3 promoters, and the promoter of BAT1 was replaced by the TDH3 promoter (AG1 pTDH3-BAT1 ura3-strain) was obtained. The 5-FOA plate medium was prepared as follows.

[Composition of 5-FOA plate medium]

| Pouched yeast growth medium SD/-Ura Broth | 2 Pouches |

[Composition of 5-FOA plate medium]

| Uracil | 50 mg |
| 5-FOA | 1 g |
| 10 × YNB | 100 mL |
| Bacto agar | 20 g |
| MilliQ Water | up to 1 L |
| | 1 L |

A mixture of pouched yeast growth medium SD/-Ura Broth (Clontech), uracil, 5-FOA, and 10×YNB diluted to 500 mL with MilliQ water and sterilized by filter sterilization, and Bacto agar diluted to 500 mL with MilliQ water and sterilized by autoclaving were mixed to prepare the 5-FOA plate medium.

Then, according to the method of Sofyanovich et al. again, a strain corresponding to the AG1 pTDH1-BAT1 ura3-strain obtained by the aforementioned method in which the promoter of the serine deaminase gene (CHA1) was replaced with pTDH3, which is a constitutive expression promoter, was prepared. The method was as follows. The AG1 pTDH3-BAT1 ura3-strain is a URA3 gene-deficient strain, and shows uracil auxotrophy. PCR was performed by using the primer of SEQ ID NO: 3

(5'-GAGTACTAATCACCGCGAACGGAAACTAATGAGTCCTCTGCGCGG

AGACATGATTCCGCATGGGCGGCTCCTGTTAAGCCTCTTAACCCAACTG

CACAGA-3')

having an upstream sequence of CHA1 at the 5' end, the primer of SEQ ID NO: 4

(5'-TATTTCAAGAAAAATTGTGCAGAAGCCTTTCCGGGGAAGAATTGA

CGTAATAATGGTGTTTTATTGTAGACTATCGACATTTGTTTATGTGTGT

TTATTC-3')

having an internal partial sequence of ORF of the CHA1 gene starting from the start codon, and the pUC19-URA3-pTDH3-URA3 plasmid as the template to obtain a DNA fragment having URA3 flanked with TDH3 promoters. The conditions for PCR were 94° C. for 10 sec (thermal denaturation), 60° C. for 10 sec (annealing), and 72° C. for 4 min (extension) for 25 cycles. The AG1 pTDH1-BAT1 ura3-strain was transformed with this DNA fragment, and applied to an SD plate medium not containing uracil. From the grown transformants, a strain in which the CHA1 promoter was replaced by pTDH3-URA3-pTDH3 was obtained. The strain in which the CHA1 promoter was replaced by pTDH3-URA3-pTDH3 was cultured overnight in the SD medium containing uracil, and applied in an appropriate amount to the 5-FOA plate medium. From the grown colonies, a strain in which URA3 was eliminated by the homologous recombination of the introduced two TDH3 promoters, and the promoter of CHA1 was replaced by the TDH3 promoter (AG1 pTDH3-BAT1 pTDH3-CHA1 ura3-strain) was obtained.

Then, according to the method of Sofyanovich et al. again, a strain corresponding to the AG1 pTDH3-BAT1 pTDH3-CHA1 ura3-strain obtained by the aforementioned method in which the promoter of the threonine deaminase gene (ILV1) was replaced with pTDH3, which is a constitutive expression promoter, was prepared. The method was as follows. The AG1 pTDH3-BAT1 pTDH3-CHA1 ura3-strain is a URA3 gene-deficient strain, and shows uracil auxotrophy. PCR was performed by using the primer of SEQ ID NO: 5

(5'-CTCTTTATTGCATATTATCTCTGCTATTTTGTGACGTTCAATTTT

AATTGACGCGAAAAAGAAAAAATAAGAAGGGCAAATCTTAACCCAACTG

CACAGA-3')

having an upstream sequence of ILV1 at the 5' end, the primer of SEQ ID NO 6

(5'-AGGTTCAATCCAGACACTTTGGACTGTTTACCTTGCCGAACAACC

GTACATAATGGTTGCTTTAGTAGAGTAGCTGACATTTGTTTATGTGTGT

TTATTC-3')

having an internal partial sequence of ORF of the ILV1 gene starting from the start codon, and the pUC19-URA3-pTDH3-URA3 plasmid as the template to obtain a DNA fragment having URA3 flanked with TDH3 promoters. The conditions for PCR were 94° C. for 10 sec (thermal denaturation), 60° C. for 10 sec (annealing), and 72° C. for 4 min (extension) for 25 cycles. The AG1 pTDH3-BAT1 pTDH3-CHA1 ura3-strain was transformed with this DNA fragment, and applied to the SD plate medium not containing uracil. From grown transformants, a strain in which the ILV1 promoter was replaced by pTDH3-URA3-pTDH3 was obtained. The strain in which the ILV1 promoter was replaced by pTDH3-URA3-pTDH3 was further cultured overnight in the SD medium containing uracil, and applied in an appropriate amount to the 5-FOA plate medium. From the grown colonies, a strain in which URA3 was eliminated by the homologous recombination of the introduced two TDH3 promoters, and the promoter of ILV1 was replaced by the TDH3 promoter (AG1 pTDH3-BAT1 pTDH3-CHA1 pTDH3-ILV1 ura3-strain) was obtained. This strain is henceforth referred to as M007Y-ura3a strain, and a strain obtained by complementing the M007Y-ura3Δ0 strain with the URA3 gene in a conventional manner (Japanese Patent Laid-open (Kokai) No. 2012-213376) is referred to as M007Y strain.

By using the M007Y-ura3a strain as the parent strain, and according to the method of Sofyanovich et al. again, a strain in which the promoter of the acetolactate synthase gene (ILV2) was replaced with the promoter of the galactokinase gene (GAL1) (henceforth also referred to as pGAL1), which is galactose-inducible, was prepared. The method was as follows. PCR was performed by using the primer of SEQ ID NO: 7

(5'-TATCTGGTTGATATATATGCTATCATTTATTTTCTTATCAAGTTT

CCAAATTTCTAATCCTTTCTCCACCATCCCTAATTCTTAACCCAACTGC

ACAGA-3')

having an upstream sequence of ILV2 at the 5' end, the primer of SEQ ID NO: 8

(5'-GGTGTGTTGCGGTATGCTATATGTTGAAAGCAACGCTTAATAGCG

AAGTTTTTTAGCGTAGATTGTCTGATCATGTTTTTTCTCCTTGACGTTA

AAGTA-3')

having an internal partial sequence of ORF of the ILV2 gene starting from the start codon, and the pUC19-URA3-pGAL1-URA3 plasmid (described in the aforementioned report of Sofyanovich) as the template to obtain a DNA fragment having URA3 flanked with GAL1 promoters. The conditions for PCR were 94° C. for 10 sec (thermal denaturation), 60° C. for 10 sec (annealing), and 72° C. for 4 min (extension) for 25 cycles. The M007Y-ura3Δ0 strain was transformed with this DNA fragment, and applied to an SG plate medium not containing uracil. From grown transformants, a strain in which the ILV2 promoter was replaced by pGAL1-URA3-pGAL1 was obtained. The preparation method of the SG medium is shown below. The SG plate medium was prepared by adding 2% of Bacto agar to the SG medium.

| [Composition of SG medium] | |
| --- | --- |
| D(+)-galactose | 20 g |
| 10 × YNB | 100 mL |
| MilliQ water | up to 1 L |
| | 1 L |

The SG medium was prepared by mixing glucose sterilized by autoclaving and YNB sterilized by filter sterilization in the aforementioned composition, and diluting the mixture with MilliQ water sterilized by autoclaving to the total volume.

Then, the strain in which the ILV2 promoter was replaced by pGAL1-URA3-pGAL1 was cultured overnight in the SG medium containing uracil, and applied in an appropriate amount to the 5-FOA plate medium. From the grown colonies, a strain in which URA3 was eliminated by the homologous recombination of the introduced two GAL1 promoters, and the promoter of ILV2 was replaced by the GAL1 promoter (AG1 pTDH3-BAT1 pTDH3-CHA1 pTDH3-ILV1 pGAL1-ILV2 ura3-strain) was obtained. This strain is henceforth referred to as M013Y-ura3Δ0 strain, and a strain obtained by complementing the M013Y-ura3Δ0 strain with the URA3 gene in a conventional manner is referred to as M013Y strain.

<Example 2> Analysis of ILV2 Gene mRNA Expression Amount and Amounts of Abu-Related Compounds in M007Y Strain and M013Y Strain (1) Culture and Sampling The M007Y strain and M013Y strain constructed in Example 1 were each inoculated in an amount of one loop into the SD medium (50 mL) contained in a 500 mL-volume Sakaguchi flask, and cultured at 30° C. for 24 hours with shaking at 120 rpm.

Absorbance of the obtained each culture broth was measured, and the culture broth was inoculated into the SD medium (70 mL) contained in a 500 mL-volume Sakaguchi flask at an OD600 of 0.01, and culture was performed at 30° C. for about 18 hours with shaking at 120 rpm (main culture). The absorbance was measured by using DU640 SPECTROPHTOMETER (BECKMAN COULTER). When OD600 became 1.5, the culture broth was sampled.

(2) Analysis of ILV2 mRNA Expression Amounts of M007Y Strain and M013Y Strain

The cells contained in the culture broth (4 mL) obtained by the aforementioned method were collected by centrifugation. The supernatant was removed as much as possible, and the cells were suspended in water (1 mL). The cells were collected again by centrifugation, and suspended in water (1 mL). This procedure was repeated twice, and the total RNA was collected from the obtained yeast cells by using RNeasy Mini Kit (QIAGEN). Reaction was allowed with 500 ng of the extracted RNA at 37° C. for 15 minutes by using PrimeScript RT Reagent Kit (Takara Bio) to prepare cDNA. Separately, for use as a negative control in RT-PCR, a sample was prepared by performing the reaction without adding reverse transcriptase.

Then, a reaction mixture was prepared by using Power SYBR Green (Applied Biosystem). For the detection of cDNA of ILV2, the primers of SEQ ID NOS: 9 and 10 were used. Further, cDNA of ACT1 was amplified by using the primers of SEQ ID NOS: 11 and 12, and used as the internal standard. The cDNA solutions of four kinds of different dilution ratios, 10, 50, 100, and 500-fold, were used. For RT-PCR, 7500 Real Time PCR System (Applied Biosystems) was used.

As a result of quantitative RT-PCR performed by the method described above, it was revealed that the ILV2 mRNA expression amount was reduced in the M013Y strain in which the ILV2 promoter was replaced, as compared with the M007Y strain as the parent strain, as shown in FIG. 1. On the basis of this result, it was confirmed that, in the M013Y strain in which the ILV2 promoter was replaced, expression from the GAL1 promoter was not induced and thus expression of ILV2 mRNA was suppressed in the SD medium containing glucose as the carbon source.

(3) Analysis of Contained Amounts of Abu, γ-Glu-Abu and γ-Glu-Abu-Gly in Cells of M007Y Strain and M013Y Strain From the obtained culture broth, the cells in an amount of 40 OD units (amount of cells contained in 1 mL of culture broth showing an OD600 of 1 is defined as 1 OD unit) were collected by centrifugation. The supernatant was removed as much as possible, and the remained cells were suspended in MilliQ water (45 mL). The cells were collected again by centrifugation, and re-suspended in MilliQ water (45 mL). By repeating this procedure 3 times in total, the medium components were completely removed from the cells. The obtained washed cells were suspended in MilliQ water (about 1.5 mL), and heated at 70° C. for 10 minutes. The extractable components contained in the cells were extracted by this process. Then, a fraction containing the extracted components and the cell residues were separated by centrifugation.

Cell debris were removed from the fraction containing the extracted components using a centrifugal filtration membrane of 10 kDa cutoff (Amicon Ultra—0.5 mL 10K, MILLIPORE, Catalogue Number UFC501096), and the obtained filtrate was used as an analysis sample.

As for the measurement of the contained amounts of Abu, γ-Glu-Abu, and γ-Glu-Abu-Gly in the sample, these compounds in the sample were derivatized with the AQC reagent and measured by LC-MS/MS according to the known method (WO2011/129462, Example 1). The differences of the measurement conditions from those of WO2011/129462, Example 1 were as follows.

Difference 1: As the 5 μM internal standard substance used for the derivatization of the sample, a standard solution consisting of 5 μM 3-methyl-His-d2 (labeled with stable isotope, Sigma) and 5 μM Gly-d2 (labeled with stable isotope, Sigma) was used.

Difference 2: The masses shown in Table 1 mentioned below were used for the selected ion in the mass spectrometer.

Difference 3: As the internal standard substance for performing quantification, there was used a derivative of 3-methyl-His-d3 for the measurement of Abu derivative, and a derivative of Gly-d2 for the measurement of γ-Glu-Abu or γ-Glu-Abu-Gly derivative. When a contaminant peak was very rarely observed in the quantification of γ-Glu-Abu depending on the sample, the quantification was performed by changing the selected ion used in the second mass analyzer to 145.2 or 104.1.

TABLE 1

| Derivative | First mass analyzer (Q1) | Second mass analyzer (Q3) |
|---|---|---|
| Abu | 274.2 | 171.1 |
| γ-Glu-Abu | 403.4 | 171.1 |
| γ-Glu-Abu-Gly | 460.4 | 171.1 |
| Gly-d2 | 248 | 171.1 |

The dry cell weight was measured for cells washed and then dried at 104° C. for 4 hours.

The concentrations of Abu, γ-Glu-Abu, and γ-Glu-Abu-Gly contained in a predetermined volume of the culture broth were divided with dry cell weights to calculate the contained amounts of Abu, γ-Glu-Abu, and γ-Glu-Abu-Gly per unit weight of dry cell weight.

As a result, as shown in FIG. 2, increased contained amounts of Abu, γ-Glu-Abu, and γ-Glu-Abu-Gly in the cells were observed for the M013Y strain as compared with the parent strain, M007Y strain. As described above, it was revealed that by attenuating the acetolactate synthase enzyme activity of yeast, the contained amounts of Abu, γ-Glu-Abu, and γ-Glu-Abu-Gly in the yeast cells could be increased. Further, in this example, for both the strains, OD600 of 1.5 was obtained in the main culture after 15 hours of the culture, and deterioration of growth due to attenuation of acetolactate synthase gene expression was not observed. On the basis of detailed analysis, it was estimated that two or more copies of the ILV2 gene existed in the M007Y strain.

<Example 3> Construction of M014Y Strain with Further Attenuated Acetolactate Synthase Gene (ILV2) Expression As described above, it was estimated that the M007Y strain contains two or more copies of the ILV2 gene. Therefore, an additional copy of the ILV2 gene in the M013Y strain as the parent strain was disrupted by the following method to prepare a strain in which the acetolactate synthase activity was further reduced (M014Y).

(1) Construction of ILV2 Gene-Disrupted Strain

A DNA fragment containing the URA3 gene was amplified by PCR using the primer of SEQ ID NO: 13

(5'-GTTACAATAGAAAGTATTTTACAAAATCTAAACCCTTTGAGCTAA

GAGGAGATAAATACAACAGAATCAATTTTCAAAAGGGCAACGGTTCATC

ATC-3')

containing 80-nucleotide upstream sequence from the start codon of ILV2, the primer of SEQ ID NO: 14

(5'-TATAAGAAGCACGATTAAATAATAATAAAGTCTGCATTTTTTACT

GAAAATGCTTTTGAAATAAATGTTTTTGAAATATTAGATATATATACGC

CAG-3')

containing 80-nucleotide downstream sequence from the stop codon of ILV2, and the genomic DNA of the *Saccharomyces cerevisiae* S288C strain as the template. The S288C strain is preserved at the independent administrative agency, National Institute of Technology and Evaluation, Biological Resource Center (NITE Biological Resource Center (NBRC)), 2-5-8 Kazusakamatari, Kisarazu-shi, Chiba-ken, 292-0818, Japan with an accession number of NBRC 1136, and can be provided therefrom. This strain is also preserved at the American Type Culture Collection (12301 Parklawn Drive, Rockville, Md. 20852, United States of America) with the accession number of ATCC 26108, and can be provided therefrom. The PCR conditions were 94° C. for 10 sec (thermal denaturation), 50° C. for 10 sec (annealing), and 72° C. for 3 min (extension) for 30 cycles. The M013Y-ura3Δ0 strain was transformed with the obtained DNA fragment, and applied to an SD plate medium not containing uracil. From the grown transformants, a strain deficient in the ILV2 gene (AG1 pTDH3-BAT1 pTDH3-CHA1 pTDH3-ILV1 pGAL1-ILV2 ilv2::URA3 strain) was obtained. This strain is henceforth referred to as M014Y strain.

(2) Confirmation of Isoleucine and Valine Auxotrophy of M014Y Strain

The M007Y strain and M013Y strain constructed in Example 1, and the M014Y strain constructed in this example were each inoculated on the SD plate medium not containing valine or isoleucine, and growth was evaluated. As a result, it was revealed that the M007Y strain and the M013Y strain could grow, whereas the M014Y strain could not grow (Table 2). That is, it was confirmed that the M014Y strain became auxotrophic for isoleucine and valine due to the disruption of ILV2.

TABLE 2

| Strain | Growth on SD plate medium |
| --- | --- |
| M007Y (parent strain) | Growable |
| M013Y (ILV2 promoter-substituted strain) | Growable |
| M014Y (ILV2 gene-disrupted strain) | Ungrowable |

<Example 4> Analysis of ILV2 Gene mRNA Expression Amount and Amounts of Abu-Related Compounds in M014Y Strain (1) Culture and Sampling The M014Y strain (ILV2-disrupted strain) constructed in Example 3, and the M007Y strain (parent strain) and M013Y (ILV2 promoter-substituted strain) constructed in Example 1 were each inoculated in an amount of one loop into the SD medium (50 mL) containing isoleucine and valine, contained in a 500 mL-volume Sakaguchi flask, and cultured at 30° C. for 24 hours with shaking at 120 rpm. Absorbance of the obtained each culture broth was measured, and the culture broth was inoculated into the SD medium (70 mL) contained in a 500 mL-volume Sakaguchi flask at an initial OD600 of 0.01, and culture was performed at 30° C. and 120 rpm. The absorbance was measured by using DU640 SPECTROPHTOMETER (BECKMAN COULTER). When OD600 became 1.5, the culture broth was sampled. The OD600 became 1.5 after 18 hours of the culture in the cases of the M007Y strain and the M013Y strain, and 47 hours of the culture in the case of the M014Y strain.

(2) Analysis of ILV2 mRNA Expression Amount in M014Y Strain

The ILV2 mRNA expression amount was analyzed in the M007Y strain, M013Y strain, and M014Y strain in the same manner as that of Example 2, (2). As a result, as shown in FIG. 3, the ILV2 mRNA expression amount of the M014Y strain was markedly smaller than those of the M007Y strain and M013Y strain.

(3) Analysis of Contained Amounts of Abu, γ-Glu-Abu, and γ-Glu-Abu-Gly in Cells of M014Y Strain The contained amounts of Abu, γ-Glu-Abu, and γ-Glu-Abu-Gly contents in the cells of the M007Y strain, M013Y strain, and M014Y strain were measured in the same manner as that of Example 2, (3). As a result, as shown in FIG. 4, the contained amounts of these compounds in the cells of the M014Y strain were markedly higher than those of the M007Y strain and M013Y strain. That is, it was revealed that the accumulation amounts of Abu, γ-Glu-Abu, and γ-Glu-Abu-Gly in yeast cells were markedly increased by decreasing the activity of acetolactate synthase.

<Example 5> Evaluation of Obtained Strains by Culture in SDTE Medium

Then, SDTE medium was designed for evaluating the M007Y strain, M013Y strain, and M014Y strain. The SDTE medium was prepared as follows.

| [Composition of SDTE medium] | |
| --- | --- |
| D(+)-glucose | 20 g |
| Thr | 1 g |
| Glu | 1 g |
| 10 × YNB (-ammonium sulfate) | 100 mL |
| Water | up to 1 L |
| | 1 L |

10×YNB (-ammonium sulfate) was prepared as follows. Difco Yeast Nitrogen Base w/o Amino Acids and Ammonium Sulfate (17 g) was dissolved in MilliQ water (1 L), and the solution was adjusted to pH 5.2, and sterilized by filter sterilization. When it was stored, it was kept in a cool dark place.

The M007Y strain and M013Y strain constructed in Example 1, and the M014Y strain constructed in Example 3 were each cultured in a medium obtained by adding isoleucine and valine to the above SDTE medium, and the contained amounts of the Abu-related compounds in the cells were measured in the same manner as that of Example 2, (3). As a result, the contained amounts of Abu, γ-Glu-Abu, and γ-Glu-Abu-Gly in the cells of the M014Y strain were markedly higher than those of the M007Y strain and M013Y strain (FIG. 5). This result revealed that reduction of the acetolactate synthase activity is effective for accumulation of Abu, γ-Glu-Abu, and γ-Glu-Abu-Gly in yeast cells, irrespective of the medium conditions.

<Example 6> Construction of Strain without Enhanced 2-Aminobutyric Acid Biosynthesis Enzyme Activity but with Attenuated Expression of Acetolactate Synthase Gene (ILV2)

In Example 4, it was revealed that modification for reducing the acetolactate synthase activity in M014Y strain, which is yeast modified so that the activities of 2-aminobutyric acid biosynthesis enzymes (α-ketobutyric acid synthetase and aminotransferase) and γ-glutamylcysteine synthetase activity were increased, markedly increased the accumulation amounts of Abu, γ-Glu-Abu, and γ-Glu-Abu-Gly in the yeast cells. Therefore, in this example, it was examined whether the contained amounts of Abu, γ-Glu-Abu, and γ-Glu-Abu-Gly were increased in yeast cells only by reducing the acetolactate synthase activity, without enhancing the activities of 2-aminobutyric acid biosynthesis pathway enzymes and γ-glutamylcysteine synthetase.
(1) Construction of ILV2 Gene-Disrupted Strain A strain corresponding to the *Saccharomyces cerevisiae* Y006 strain (FERN BP-11299) of which acetolactate synthase gene (ILV2) was disrupted was prepared by the following method for the purpose of reducing the acetolactate synthase activity.

First, a region containing ILV2 replaced by the kanamycin resistance gene cassette KanMX was amplified by PCR using the primers of SEQ ID NO: 25

(GACAGTAAAACGCAGGTTAT)

and SEQ ID NO: 26

(TCTAGAAGAGTTGTTATTTC), and the genome of the ILV2 disrupted-strain of YEAST KNOCK OUT STRAIN COLLECTION (Funakoshi, YCS1056). The PCR conditions were 94° C. for 10 sec (thermal denaturation), 50° C. for 10 sec (annealing), and 72° C. for 3 min (extension) for 25 cycles. Then, the thus-amplified DNA fragment was purified by ethanol precipitation, and used to transform the Y006 strain, and the cells were applied to the YPD plate medium containing G418. From the grown transformants, a strain in which the ILV2 gene was replaced by KanMX (ILV2::KanMX strain) was obtained. This strain is henceforth referred to as M015Y strain. The preparation method of the YPD medium is shown below. The YPD plate medium was prepared by adding 2% of Bacto agar to the YPD medium.

| [Composition of YPD medium] | |
|---|---|
| D(+)-glucose | 20 g |
| Yeast extract | 10 g |
| Polypeptone | 20 g |
| MilliQ Water | up to 1 L |
| | 1 L |

The medium was used after addition of G418 disulfate (Sigma) at a concentration of 200 mg/L.
(2) Confirmation of Auxotrophy for Isoleucine and Valine of M015Y Strain The M015Y strain constructed in this example and the parent strain thereof, Y006 strain, were each inoculated on an SD plate medium not containing valine or isoleucine, and growth was evaluated. As a result, it was revealed that the Y006 strain could grow, whereas the M015Y strain could not grow (Table 3). That is, it was confirmed that the M015Y strain became auxotrophic for isoleucine and valine due to the disruption of ILV2.

TABLE 3

| Strain | Growth on SD plate medium |
|---|---|
| Y006 (parent strain) | Growable |
| M015Y (ILV2 gene-disrupted strain) | Ungrowable |

<Example 7> Evaluation of M015Y Strain by Culture in SD Medium and SDTE Medium

Then, the M015Y strain and Y006 strain were each cultured in media obtained by adding isoleucine and valine to the SD medium and SDTE medium, and the contained amounts of Abu-related compounds in the cells were measured in the same manner as that of Example 2, (3). As a result, in the case of the culture in the SD medium, the contained amounts of Abu and γ-Glu-Abu in the cells of the M015Y strain were markedly higher than those of the parent strain, Y006 strain (FIG. 6). In the case of the culture in the SDTE medium, increases in Abu, γ-Glu-Abu, and γ-Glu-Abu-Gly contents were observed (FIG. 7). On the basis of these results, it was revealed that, also in yeast not modified so that the activities of 2-aminobutyric acid biosynthetic pathway enzymes (α-ketobutyric acid synthetase and aminotransferase) and γ-glutamylcysteine synthetase activity increase, reduction of the acetolactate synthase activity is effective for accumulation of Abu, γ-Glu-Abu, and/or γ-Glu-Abu-Gly in yeast cells.

INDUSTRIAL APPLICABILITY

According to the present invention, yeast and a yeast extract with a high content of Abu, γ-Glu-Abu, and/or γ-Glu-Abu-Gly are provided.

EXPLANATION OF SEQUENCE LISTING

SEQ ID NOS: 1 to 14, Primers
SEQ ID NO: 15, Nucleotide sequence of ILV2 gene of *Saccharomyces cerevisiae* S288C
SEQ ID NO: 16, Amino acid sequence of Ilv2 protein of *Saccharomyces cerevisiae* S288C
SEQ ID NO: 17, Nucleotide sequence of CHA1 gene of *Saccharomyces cerevisiae* S288C
SEQ ID NO: 18, Amino acid sequence of Cha1 protein of *Saccharomyces cerevisiae* S288C
SEQ ID NO: 19, Nucleotide sequence of ILV1 gene of *Saccharomyces cerevisiae* S288C
SEQ ID NO: 20, Amino acid sequence of Ilv1 protein of *Saccharomyces cerevisiae* S288C
SEQ ID NO: 21, Nucleotide sequence of BAT1 gene of *Saccharomyces cerevisiae* S288C
SEQ ID NO: 22, Amino acid sequence of Bat1 protein of *Saccharomyces cerevisiae* S288C
SEQ ID NO: 23, Nucleotide sequence of GSH1 gene of *Saccharomyces cerevisiae* S288C
SEQ ID NO: 24, Amino acid sequence of Gsh1 protein of *Saccharomyces cerevisiae* S288C
SEQ ID NOS: 25 and 26, Primers

The invention claimed is:

1. Yeast, comprising:
   60 μmol/g-DCW or more of an α-aminobutyric acid (Abu)-related compound consisting of at least one compound selected from the group consisting of Abu, γ-Glu-Abu, and γ-Glu-Abu-Gly,
   wherein the yeast is *Saccharomyces cerevisiae* and has been modified such that intracellular activity of acetolactate synthase encoded by ILV2 gene in the yeast is decreased to 10% or less of intracellular activity of a corresponding enzyme in the wild type of the yeast, and that the yeast has increased activity of at least one of α-ketobutyric acid synthase and aminotransferase as compared to the wild type of the yeast,
   wherein the α-ketobutyric acid synthase is selected from the group consisting of:
   (a) a protein comprising the amino acid sequence of SEQ ID NO: 18;
   (b) a protein comprising a variant of the amino acid sequence of SEQ ID NO: 18, which has substitution, deletion, insertion, or addition of 1 to 10 amino acid residues in the amino acid sequence of SEQ ID NO: 18, and having α-ketobutyric acid synthase activity; and
   (c) a protein comprising an amino acid sequence having an identity of 90% or higher to the amino acid sequence of SEQ ID NO: 18, and having α-ketobutyric acid synthase activity, and
   wherein the aminotransferase is selected from the group consisting of:
   (d) a protein comprising the amino acid sequence of SEQ ID NO: 22;
   (e) a protein comprising a variant of the amino acid sequence of SEQ ID NO: 22, which has substitution, deletion, insertion, or addition of 1 to 10 amino acid residues in the amino acid sequence of SEQ ID NO: 22, and having aminotransferase activity; and
   (f) a protein comprising an amino acid sequence having an identity of 90% or higher to the amino acid sequence of SEQ ID NO: 22, and having aminotransferase activity.

2. The yeast according to claim 1, wherein the α-ketobutyric acid synthetase is an enzyme encoded by CHA1 gene.

3. The yeast according to claim 1, wherein the aminotransferase is an enzyme encoded by BAT1 gene.

4. The yeast according to claim 1, wherein the yeast has been further modified so that activity of γ-glutamylcysteine synthetase is increased.

5. A method for producing a yeast extract, the method comprising:
   preparing a yeast extract from a raw material comprising the yeast according to claim 1.

6. A method for producing an Abu-related compound, the method comprising:
   culturing the yeast according to claim 1 in a medium; and
   collecting the Abu-related compound from the cultured yeast.

7. The method according to claim 6, wherein the Abu-related compound is at least one of γ-Glu-Abu and γ-Glu-Abu-Gly.

8. The yeast according to claim 1, wherein the yeast comprises 140 μmol/g-DCW or more of the Abu-related compound.

9. The yeast according to claim 1, wherein the ILV2 gene has the nucleotide sequence of SEQ ID NO: 15 or a nucleotide sequence having not less than 95% homology to the nucleotide sequence of SEQ ID NO: 15.

10. The yeast according to claim 1, wherein the activity of the at least one of α-ketobutyric acid synthase and aminotransferase is increased by increasing a copy number of a gene encoding the at least one of α-ketobutyric acid synthase and aminotransferase, replacing a promoter of the gene with a stronger promoter, replacing a rare codon present in the gene with a synonymous codon with higher frequency, amplifying a regulator capable of increasing expression of the gene, or deleting or attenuating a regulator capable of reducing expression of the gene, or a combination thereof.

11. The yeast according to claim 1, wherein the α-ketobutyric acid synthetase is an enzyme encoded by CHA1 gene, and the aminotransferase is an enzyme encoded by BAT1 gene.

12. The yeast according to claim 11, wherein the yeast comprises 140 μmol/g-DCW or more of the Abu-related compound.

13. The yeast according to claim 11, wherein the ILV2 gene has the nucleotide sequence of SEQ ID NO: 15 or a nucleotide sequence having not less than 95% homology to the nucleotide sequence of SEQ ID NO: 15.

14. The yeast according to claim 11, wherein the activity of the at least one of α-ketobutyric acid synthase and aminotransferase is increased by increasing a copy number of a gene encoding the at least one of α-ketobutyric acid synthase and aminotransferase, replacing a promoter of the gene with a stronger promoter, replacing a rare codon present in the gene with a synonymous codon with higher frequency, amplifying a regulator capable of increasing expression of the gene, or deleting or attenuating a regulator capable of reducing expression of the gene, or a combination thereof.

15. The yeast according to claim 2, wherein the yeast comprises 140 μmol/g-DCW or more of the Abu-related compound.

16. The yeast according to claim 2, wherein the ILV2 gene has the nucleotide sequence of SEQ ID NO: 15 or a nucleotide sequence having not less than 95% homology to the nucleotide sequence of SEQ ID NO: 15.

17. The yeast according to claim 2, wherein the activity of the at least one of α-ketobutyric acid synthase and aminotransferase is increased by increasing a copy number of a gene encoding the at least one of α-ketobutyric acid synthase and aminotransferase, replacing a promoter of the gene with a stronger promoter, replacing a rare codon present in the gene with a synonymous codon with higher frequency, amplifying a regulator capable of increasing expression of the gene, or deleting or attenuating a regulator capable of reducing expression of the gene, or a combination thereof.

18. The yeast according to claim 3, wherein the yeast comprises 140 μmol/g-DCW or more of the Abu-related compound.

19. The yeast according to claim 3, wherein the ILV2 gene has the nucleotide sequence of SEQ ID NO: 15 or a nucleotide sequence having not less than 95% homology to the nucleotide sequence of SEQ ID NO: 15.

20. The yeast according to claim 3, wherein the activity of the at least one of α-ketobutyric acid synthase and aminotransferase is increased by increasing a copy number of a gene encoding the at least one of α-ketobutyric acid synthase and aminotransferase, replacing a promoter of the gene with a stronger promoter, replacing a rare codon present in the gene with a synonymous codon with higher frequency, amplifying a regulator capable of increasing expression of the gene, or deleting or attenuating a regulator capable of reducing expression of the gene, or a combination thereof.

* * * * *